(12) United States Patent
Lin et al.

(10) Patent No.: US 9,387,251 B2
(45) Date of Patent: Jul. 12, 2016

(54) SUGAR ALCOHOL-BASED COMPOSITIONS FOR DELIVERING NUCLEIC ACID-BASED DRUGS IN VIVO AND IN VITRO

(71) Applicants: Shi-Lung Lin, Arcadia, CA (US); David T S Wu, Arcadia, CA (US)

(72) Inventors: Shi-Lung Lin, Arcadia, CA (US); Yi-Wen Lin, Cerritos, CA (US)

(73) Assignees: Shi-Lung Lin, Arcadia, CA (US); David TS Wu, Arcadia, CA (US)

( * ) Notice: Subject to any disclaimer, the term of this patent is extended or adjusted under 35 U.S.C. 154(b) by 0 days.

(21) Appl. No.: 14/457,829

(22) Filed: Aug. 12, 2014

(65) Prior Publication Data

US 2014/0350085 A1   Nov. 27, 2014

Related U.S. Application Data

(63) Continuation-in-part of application No. 14/142,512, filed on Dec. 27, 2013, and a continuation-in-part of application No. 13/572,263, filed on Aug. 10, 2012, now abandoned.

(60) Provisional application No. 61/931,650, filed on Jan. 26, 2014.

(51) Int. Cl.
| | |
|---|---|
| *A61K 47/26* | (2006.01) |
| *A61K 31/713* | (2006.01) |
| *A61K 31/7105* | (2006.01) |
| *C12N 15/11* | (2006.01) |
| *C12N 15/113* | (2010.01) |

(52) U.S. Cl.
CPC .............. *A61K 47/26* (2013.01); *A61K 31/713* (2013.01); *A61K 31/7105* (2013.01); *C12N 15/111* (2013.01); *C12N 15/113* (2013.01); *C12N 2310/141* (2013.01); *C12N 2320/32* (2013.01); *C12N 2330/50* (2013.01); *C12N 2330/51* (2013.01); *C12N 2740/15041* (2013.01)

(58) Field of Classification Search
None
See application file for complete search history.

(56) References Cited

U.S. PATENT DOCUMENTS

| | | | |
|---|---|---|---|
| 6,251,599 B1 | 6/2001 | Chen et al. | |
| 6,582,729 B1 * | 6/2003 | Eljamal ................ | A61K 9/0075 424/43 |
| 2014/0350085 A1 | 11/2014 | Lin et al. | |

FOREIGN PATENT DOCUMENTS

| | | | |
|---|---|---|---|
| WO | WO 2007/133616 | * | 11/2007 |
| WO | WO 2007/133616 A2 | | 11/2007 |

OTHER PUBLICATIONS

International Search Report and Written Opinion of the International Searching Authority, (Forms PCT/ISA/220, PCT/ISA/210 and PCT/ISA/237), mailed Nov. 17, 2014, for International Application No. PCT/US2014/050114.
Arsequell, G., et al, "9-Fluorenylmethoxycarbonyl (Fmoc)-Glycine Coupling of Saccharide β-Glycosylamines for Fractionation of Oligosaccharides and the Formation of Neoglycoconjugates," Analytical Biochemistry, Jan. 1, 1994, vol. 216, No. 1, pp. 165-170.
Chrzaszczewska, A. et al, "The diacylglycerophosphoric acids. III, Glycine esters," Acta Chim., 1962, vol. 8, pp. 29-35.
Gannon, M.C. et al., "The metabolic response to ingested glycine," Am. J. Clin Nutr., Jan. 1, 2002, vol. 76, pp. 1302-1307.
International Search Report for Appl. No. PCT/US2014/072693 dated Apr. 20, 2015.
Kinomura, K. et al., "Synthesis of Methyl-2,3-Di-O-Glycly-α-D-Glucopyranoside and 4,6-Di-O-Glycly-2,3-Di-O-Methyl-α-D-Glucopyranoside, and removal of aminoacyl groups from sugar moieties," J. Carbohydrate Chemistry, Jan. 1, 1984, vol. 3, No. 2, pp. 229-241.
Weizmann, M. et al, "Attempts to prepare esters of glycerol and amino acids, as the mixed esters of amino acids and fatty acids. 1st part." Bulletin de la Societe Chimique de France, Societe Francaise de Chimie, Jan. 1, 1932, vol. 51, No. 4, pp. 59-73.
Written Opinion of the International Searching Authority for Appl. No. PCT/US2014/072693 dated Apr. 20, 2015.

* cited by examiner

*Primary Examiner* — Doug Schultz
(74) *Attorney, Agent, or Firm* — Birch, Stewart, Kolasch & Birch, LLP

(57) ABSTRACT

This invention relates to a composition and its use for formulating nucleic acid-based drugs/vaccines with sugar alcohol compositions into complexes for both in-vitro and in-vivo delivery. Particularly, the present invention includes the ingredients and processes necessary for formulating therapeutic and pharmaceutical nucleic acid compositions, such as miRNA, microRNA precursors, shRNAs, siRNAs, ribozymes, antisense RNAs/DNAs, RNA-DNA hybrids and DNA vectors/vaccines, with glycylated sugar alcohols/sugars into delivery complexes, which can then be absorbed by cells in vivo and in vitro via active endocytosis. Also, the present invention discloses that chemical compounds containing sugar alcohol- and/or sugar-like structures can protect nucleic acids, in particular miRNAs, shRNAs, siRNAs and ribozymes, from degradation in vivo as well as in vitro. Therefore, the present invention is also a formula and method for preserving the structural integrity and functional efficacy of these nucleic acid-based drugs and/or vaccines in vivo and in vitro.

30 Claims, 14 Drawing Sheets
(10 of 14 Drawing Sheet(s) Filed in Color)

glycerol (glycerin)

glycine

*Glycylation of Sugar Alcohols (i.e. glycerol)* diglycylglycerol (DGG)

OR triglycylglyceride
(TGG)

FIG. 2B

The sequence (SEQ.ID.NO.1) of miR-302 familial cluster

```
  1  AATTTTTTTC TTCTAAAGTT ATGCCATTTT GTTTTCTTTC TCCTCAGCTC TAAATACTCT
                                                                                    miR-302b
 61  GAAGTCCAAA GAAGTTGTAT GTTGGGTGG CTCCCTTCAA CTTAACATG GAAGTGCTTT
                                                                                    miR-302c
121  CTGTGACTTT AAAGTAAGT GCTTCCATGT TTAGTAGGA GTGAATCCAA TTTACTTCTC
                                                                                    miR-302c
181  CAAAATAGAA CACGGCTAACC TCATTGAAGG GGATCCCCT TTCTTTAACA TGGGGGTACC
241  TGCTGTGTGA ACAAAGTAAG TGCTTCCA TGTTTGCAGTG GAGTTGTCTC CAAGCCAGCA
301  CACCTTTGT TACAAAATTT TTTGTGTATT GTGTTTTAAG GTTACTAAGC TTGTTACAGG
                                                                                    miR-302a
361  TTAAAGGATT CTAACTTTTT CCAAGACTGG GCTCCCCACC ACTTAAAGT GGATGTACTT
421  GCTTTGAAAC TAAAGAAGTA AGTGCTTCCA TGTTTTGGTG ATGGTAAGTC TTCTTTTAC
481  ATTTTATTA TTTTTTTACA AAATAACTTT ATTGTATTGA CCGCAGCTCA TATATTTAAG
                                                                                    miR-302d
541  CTTTATTTTG TATTTTTACA TCTGTTAAGG GGCCCCTCT ACTTAACAT GAGGCACTT
601  GCTGTGACAT GACAAAATA AGTGCTTCCA TGTTTTGAGTG TGTGGTTCC TACCTAATCA
661  GCAATTGAGT TAACGCCCAC ACTGTGTGCA GTTCTTGGCT ACAGGCCATT ACTGTGCTA
``` pre-miR-302a (SEQ.ID.NO.2)

pre-miR-302b (SEQ.ID.NO.3)

pre-miR-302c (SEQ.ID.NO.4)

pre-miR-302d (SEQ.ID.NO.5)

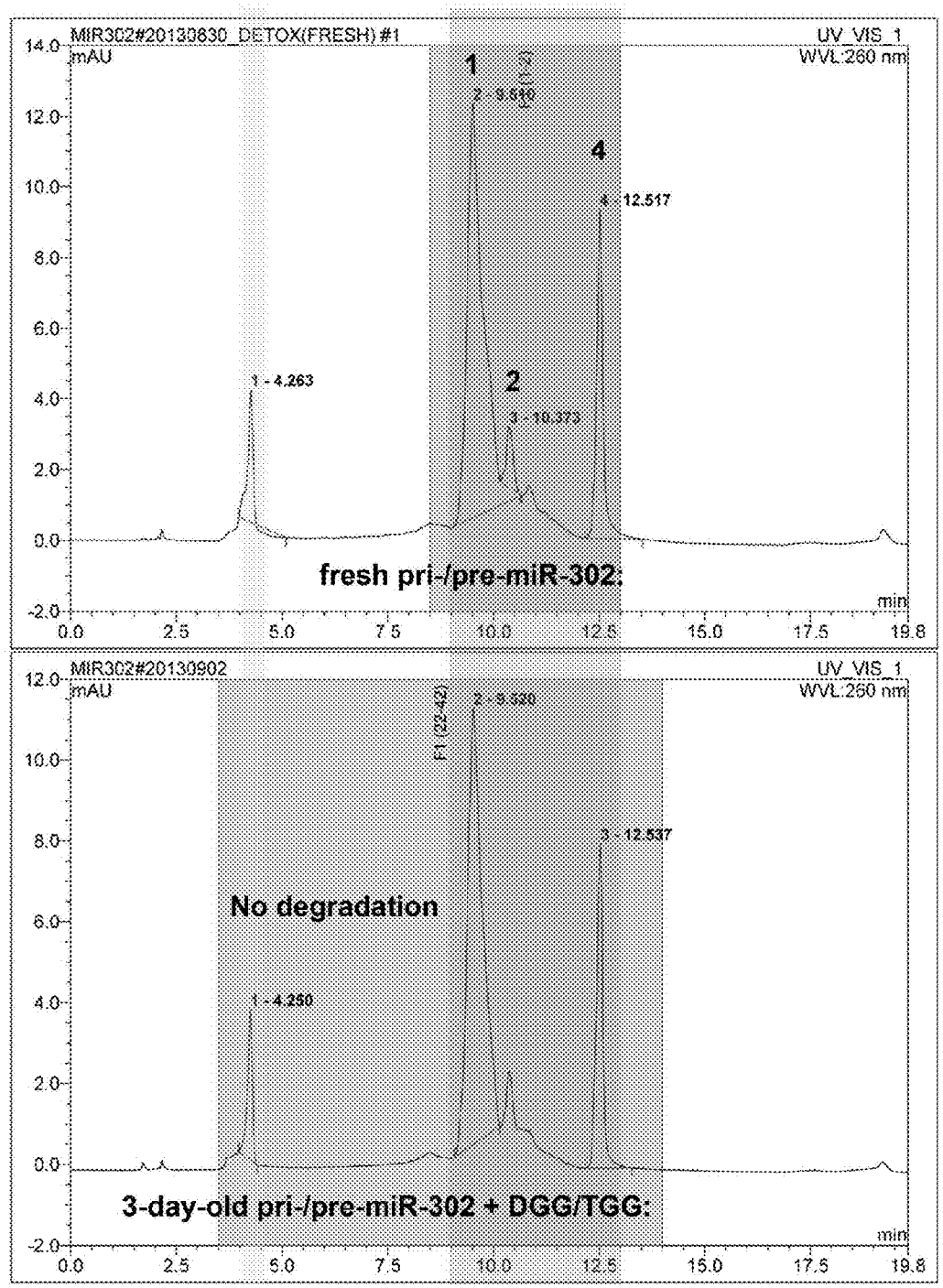

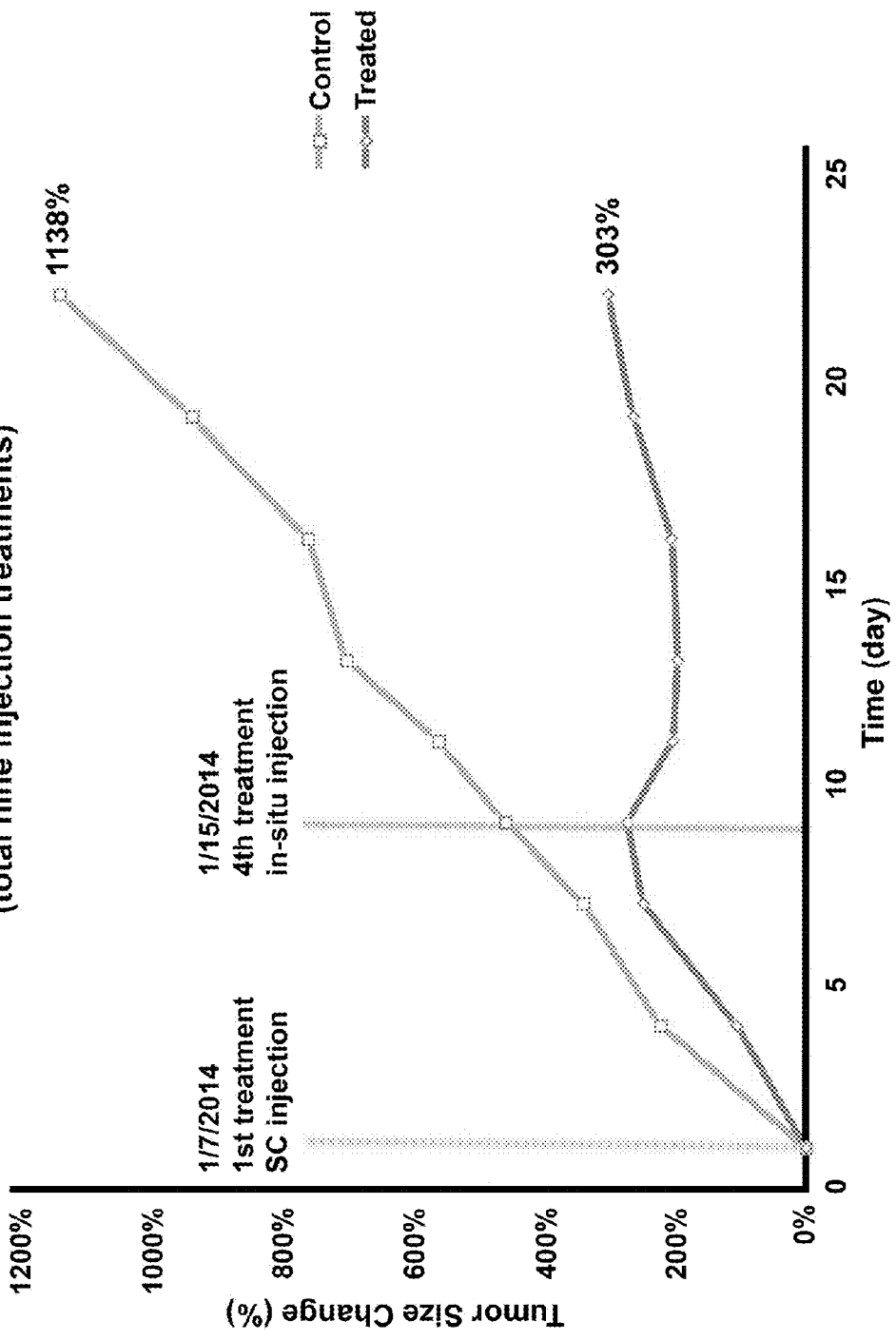

SUGAR ALCOHOL-BASED COMPOSITIONS FOR DELIVERING NUCLEIC ACID-BASED DRUGS IN VIVO AND IN VITRO

PRIORITY

The present invention claims priority to the U.S. Provisional Application Ser. No. 61/931,650 filed on Jan. 26, 2014, which was entitled "Composition and Formulation of Sugar Alcohol-Based Complexes for Delivering Nucleic Acid-Based Drugs In Vitro and In Vivo". The present invention also claims priority to the U.S. patent application Ser. No. 13/572,263 filed on Aug. 10, 2012, entitled "An Inducible Gene Expression Composition for Using Eukaryotic Pol-2 Promoter-Driven Transcription in Prokaryotes and The Applications Thereof". The present application further claims priority to the U.S. patent application Ser. No. 14/142,512 filed on Dec. 27, 2013, entitled "Production and Extraction of MicroRNA Precursors as Drugs for Cancer Therapy". The present application is a continuation-in-part (CIP) application of the U.S. patent application Ser. No. 13/572,263 filed on Aug. 10, 2012, entitled "An Inducible Gene Expression Composition for Using Eukaryotic Pol-2 Promoter-Driven Transcription in Prokaryotes and The Applications Thereof" and the U.S. patent application Ser. No. 14/142,512 filed on Dec. 27, 2013, entitled "Production and Extraction of MicroRNA Precursors as Drugs for Cancer Therapy", which are hereby all incorporated by reference as if fully set forth herein.

FIELD OF INVENTION

This invention generally relates to a novel chemical composition and its use for formulating RNA- and/or DNA-based drugs/vaccines with modified sugar alcohols and/or sugars into stable complexes for both in-vitro and in-vivo delivery. Particularly, the present invention teaches the key ingredients and processes necessary for formulating therapeutic and pharmaceutical nucleic acid compositions, such as microRNA (miRNA) and its precursors/mimics, small hairpin RNAs (shRNA), short interfering RNAs (siRNA), ribozymes, antisense RNAs/DNAs, RNA-DNA hybrids and DNA vectors/vaccines, with novel glycylated sugar alcohols into delivery complexes, which can then be absorbed by cells in vivo and in vitro via an active mechanism, such as endocytosis, for releasing the therapeutic effects of the nucleic acid compositions. The novelty of the present invention is to create positively charged sugar alcohol/sugar-containing compounds for interacting with negatively charged nucleic acid compositions via ionic and/or electrostatic affinity rather than covalent conjugation or hydrogen bonding, so as to preserve the structural integrity of the nucleic acid compositions for better delivery of their drug effects into cells in vivo and in vitro. In addition, the present invention discovered for the first time that chemical compounds like sugar alcohols and sugars can protect small functional nucleic acids, in particular miRNA, shRNA, siRNA and ribozyme molecules, from degradation in vivo as well as in vitro. Therefore, the present invention is not only a composition and its use for delivering nucleic acid-based drugs/vaccines into cells but also a formula for preserving the structural integrity and functional efficacy of these nucleic acid-based drugs and/or vaccines in vivo and in vitro.

BACKGROUND

Delivery of functional non-coding RNAs (ncRNA) such as ribozyme, microRNA (miRNA), short hairpin RNA (shRNA) and small interfering RNA (siRNA) is the major obstacle hindering the development of RNA interference (RNAi)-based therapy in vivo. Low penetration and high degradation of these ncRNAs are the problems of delivery. In order to overcome these problems, functional ncRNAs must be protected by a delivery agent that is able to not only preserve their structural integrity but also facilitate their uptake by cells in vivo. Yet, none of previously found liposomal or sugar-based delivery agents can fulfill both needs.

Nucleic acid compositions like ribonucleic acids (RNA) and deoxyribonucleic acids (DNA) are negatively charged molecules and hence tend to attract positively charged materials. On the other hand, the cell membrane consists of phospholipid bilayer, which contains abundant fatty acids and thus is also negatively charged. As a result, naked RNA/DNA will be repelled by the cell membrane and cannot be directly delivered into cells. In order to overcome this problem, one preferred traditional delivery method is liposomal transfection using lipid-based liposomes to encapsulate DNAs/RNAs for intracellular delivery. The mechanism of liposomal transfection is achieved by fusion of liposomes to the phospholipid bilayer of the cell membrane, resulting in passive diffusion of the liposome-encapsulated RNAs/DNAs into the cells. To further improve their delivery efficiency, those liposome molecules are often modified by adding long carbon chains (i.e. glycolipids) or positively charged chemical groups, or both, such as polyethylene glycol [PEG; H—(O—$CH_2$—$CH_2$)$_n$—OH] (Immordino et al, 2006), glycerol esters (WO2011143237 to Meyering), glycerol monooleate (Pereira et al, 2002; Zhen et al, 2012), and aminated/amino poly(glycerol methacrylate)s (Gao et al, 2010 and 2011). However, due to their limit by passive diffusion, the efficiency of these liposomal methods is generally not comparable to an active delivery method based on endocytosis.

In a liposomal delivery system, glycerol is often used as a polymer linker to connect the long carbon chains of fatty acids and phospholipids, such as monooleate and glycerol esters. Modifications in these long carbon chains can form charged chemical groups to interact with DNA/RNA; yet, those charged carbon chains do not possess any ability (i.e. polarity) to protect DNA/RNA from degradation. Alternatively, glycerol also can serve as a side chain in a delivery polymer, such as aminated/amino poly(glycerol methacrylate)s. Those aminated glycerol side chains in such acrylate polymers carry positively charged groups that can form hydrogen bonding (H-bond) with DNA and RNA (Gao et al, 2010). Nevertheless, it is known that the duplex and hairpin structures of DNA and RNA are also formed and maintained by H-bonds. As a result, the H-bonds formed by aminated/amino poly(glycerol methacrylate)s will disturb the structural integrity of DNA/RNA duplexes and hairpins, which are actually required for maintaining the function of many currently known nucleic acid-based drug agents, such as miRNA, shRNA, siRNA, ribozyme and DNA vaccine. Conceivably, none of these liposomal delivery systems can protect DNA and RNA from degradation.

Sugar-based delivery is another preferred transfection method, which is designed to improve the low efficiency of liposomal delivery. Sugar-encapsulated DNAs/RNAs can be absorbed by cells via an active endocytosis mechanism, which increases their concentration in cells and hence their functional efficacy as well. A variety of compositions have been used in these sugar-based delivery systems, including sugar-based surfactants (EP0535534 to Nair; WO2009029046 to Kim), poly(sugar acrylate) ploymers (U.S. Pat. No. 5,618,933 to Dordick), sugar-grafted liposomes (Banerjee et al, 1996), lipid-protein-sugar particles (WO2002032398 to Kohane et al), poly(glycosylated amino acid)s (Davis et al, 2002), lipoamino acid-/glycopeptide- and/or liposaccharide-conjugants (Blanchfield et al, 2004), pectin/chitosan/lecithin nanoparticles (Morris et al, 2010; Cuna et al, 2006; Graf et al, 2008), sugar-PEG-based polymers (Davis et al, 2010; Bhatia et al, 2011), and boron-saccharide complexes (Ellis et al, 2012). However, none of these sugar-based compositions have been reported to protect the structural integrity of RNA and DNA from degradation. Also, because polysaccharides and sugars do not normally carry any charge, many of these methods still need to be used in conjunction with liposomes in order to encapsulate DNAs/RNAs. As a result, difficult formulation is another problem.

In sum, there is currently no delivery agent that can efficiently deliver RNAs/DNAs into cells while protecting their intact strand structures, particularly duplexes and hairpins, during delivery. Moreover, since these previously developed delivery agents can not been found in any living biological system and have not been tested for in-vivo delivery yet, their safety and in-vivo efficiency are highly uncertain. Therefore, it is highly desirable to have a novel delivery system that not only safely exists in a living system but also is useful for efficiently deliver RNAs/DNAs into cells in vitro as well as in vivo while protecting their intact strand structures, in particular duplexes and hairpins.

SUMMARY OF THE INVENTION

Stem cells are like a treasure box containing numerous effective ingredients useful for designing and developing pharmaceutical and therapeutic applications, such as stimulating cell/tissue/organ regeneration, repairing and/or rejuvenating damaged/aged tissues/organs, treating degenerative diseases (i.e. diabetes, osteoporosis, Parkinson's and Alzheimer's diseases etc), and preventing tumor/cancer formation, progression and metastasis. Hence, we have used stem cells as a tool for novel drug screening, identification, isolation and production as well as studying the mechanism underlying how stem cells produce and preserve these identified drug ingredients (Chen and Lin, (2013) *Recent Patents on Regenerative Medicine* 3, 5-16). As a result, the present invention discloses for the first time that chemical compounds containing sugar alcohol- and/or sugar-like structures can protect hairpin-like RNA molecules, in particular microRNA precursors (i.e. pri- and/or pre-miRNAs), shRNAs, siRNAs and ribozymes, from degradation in human induced pluripotent stem cells (iPSC) and iPSC-derived embryoid bodies. Due to the structural similarity of all eukaryotic cells, the identified sugar alcohols/sugars may also provide the same protective effect against the degradation of these functional RNA species (i.e. microRNAs, shRNAs, siRNAs and ribozymes) in other cell types in vitro and in vivo.

Sugar alcohols are a generic kind of polyol alcohols derived from sugars and also frequently called polyhydric alcohol, polyalcohol, or glycitol. As defined in polymer chemistry, polyols are compounds with multiple active hydroxyl groups available for organic reactions and polymeric polyols are usually in a form of polyethers or polyesters. Most sugar alcohols are white, water-soluble natural occurring materials that are often used in the cosmetic, pharmaceutical and food industries as humectants, thickeners and sweeteners. They are represented by a general chemical formula $H(HCHO)_{n+1}H$, which is different from sugars' $H(HCHO)_nHCO$. Also, unlike sugars which tend to form rings, sugar alcohols do not. Yet, they can be dehydrated into cyclic ethers, e.g. sorbitol can be dehydrated to isosorbide. The sugar alcohols differ in chain length and have one hydroxyl (OH) group attached to each carbon (C) molecule in the chain. They are further differentiated by their relative orientation (stereochemistry) of these OH groups; for example, mannitol and sorbitol are isomers that share the same chemical formula $C_6H_8(OH)_6$ but are different in the orientation of the OH group on carbon 2 ($C^2$). The common types of sugar alcohols include, but not limited by, alditol, arabitol, erythritol, fucitol, galactitol, glycerol (or called glycerin), iditol, inositol, isomalt, lactitol, maltitol, mannitol, polyglycitol, sorbitol, threitol, volemitol and xylitol. For the present invention, in addition to sugar alcohols, sugars such as glucose, fructose, galactose, sucrose, and lactose can also be used; alternatively, some sugars can be used to replace sugar alcohols, such as glucose, fructose, galactose, sucrose, and lactose.

Nucleic acid molecules like deoxyribonucleic acids (DNA) and ribonucleic acids (RNA) are negatively charged materials due to the phosphodiester linkage between consecutive nucleotides and thus they tend to interact with positively charged compounds. However, ions in the water often break down this linkage structure of DNA and particularly RNA strands through a force of hydrolysis and hence cause degradation. To prevent RNA/DNA degradation, alcohol materials are known to carry strong polarity that can expel water molecules out of the strands of RNA and DNA, resulting in stabilizing the structural integrity of RNA and DNA strands. In the present invention, we have used modified sugar alcohols and polysaccharides to encapsulate functional RNAs/DNAs for in-vitro and in-vivo delivery; however, sugar alcohols and sugars usually do not carry any charge or sometimes even carry a slightly negative charge under a low pH condition and hence do not interact well with negatively charged nucleic acids. After studying microRNA miR-302 isolated from human induced pluripotent stem cells (iPSCs), we found that some novel modified sugars/sugar alcohols are always purified together with miR-302 and are required for stabilizing and protecting the hairpin structures of miR-302 precursors from degradation. To find this sugar/sugar alcohol identity, our further studies revealed that glycylation is one of the novel sugar/sugar alcohol modifications that promote and enhance the interactions between intracellular sugars/sugar alcohols and RNAs/DNAs, in particular hairpin-like microRNA precursors (i.e. pri-/pre-miRNAs). Accordingly, some other similar modifications such as glycylated amino acid-mediated glycylation and glutamylation may provide the same or similar functionality.

As shown in FIGS. 1A and 1B, a totally novel chemical reaction—glycylation of sugar alcohols—is found to be required for making positively charged sugars/sugar alcohols that form stable delivery complexes with either isolated or recombinant RNAs/DNAs and/or RNA/DNA-like synthetic molecules, which are useful for developing drugs and therapies. Previously, glycylation occurs between amino acids but not in sugars or sugar alcohols. Yet, as defined here, glycylation is a chemical reaction that replaces the hydroxyl (HO—) groups of a sugar alcohol or sugar with glycine's glycyl ($NH_2CH_2COO$—) groups and thus results in the formation of an ether (R—O—R) linkage between each OH-removed carbon of the sugar/sugar alcohol and the glycyl group. This reaction also involves a process of condensation via dehydration. For example, when glycerol (or called glycerin) is used as a model of sugar alcohol, glycylation of glycerol will generate three kinds of reactive products: one is 1-, or 2-, or 3-monoglycylglycerol (MGG), another is 1,2-, or 2,3-, or 1,3-diglycylglycerol (FIG. 1A; DGG), and the other is 1,2,3-triglycylglyceride (FIG. 1B; TGG). In this model, glycylation can be a partial or completed reaction; for example, MGG and DGG are partially glycylated products, while TGG is a completely glycylated product. All MGG, DGG and TGG are positively charged molecules that interact with negatively charged materials, such as RNA, DNA and any other kind of acidic materials, via ionic/electrostatic affinity and hence useful for intracellular delivery. Due to such charge affinity, the mixture of DNA/RNA and glycylated sugars/sugar alcohols can easily and instantly form encapsulated complexes or polymers. Like natural sugars, these modified (i.e. glycylated) sugar alcohols can be absorbed by cells via receptor-mediated endocytosis. Also, sugar alcohols/sugars with higher molecular weights may form higher degree structures of glycylation; yet, the basic function and uptake mechanism of these modified sugar alcohols/sugars are likely similar.

The reaction of glycylation of sugar alcohols/sugars has never been reported before. The present invention herein disclosed for the first time its existence, natural function and the related utilizations thereof. Since glycylated sugar alcohols/sugars can interact with all sorts of small negatively charged materials (including organic or inorganic chemical compounds and drugs) for intracellular delivery, they are useful for developing a variety of therapeutic, pharmaceutical and cosmetic products, devices as well as applications. For instance, they can be used to transduce hydroxylapatite (HA or called hydroxyapatite), filling nanoparticles, hyaluronic acids/kojic acids/ascorbic acids, arbutin, and/or anti-tyrosinase miRNAs/shRNAs/siRNAs/DNAs into epidermal skin cells for cosmetic skin lightening/whitening and/or wrinkle removal. For another example, they can be used to encapsulate and formulate functional microRNAs (i.e. pre-miRNA/shRNA) and/or their siRNA mimics as therapeutic drugs/vaccines for treating diseases. To this point, it has been known that microRNAs such as miR-34, miR-146a, miR-142-3p and miR-302 are tumor suppressors which can be used for treating various human tumors/cancers, including but not limited, liver, lung, skin, bone, prostate, breast cancers and brain tumors as well as leukemia [Lin et al., (2008) *RNA* 14:417-424; (2008) *RNA* 14:2115-2124; (2010) *Cancer Research* 70:9473-9482]. Furthermore, these sugar alcohols/sugars may be applied to protect and deliver vector-based DNA/RNA drugs and/or vaccines that are frequently used for gene therapy and anti-viral treatments. As a result, it is conceivable that the present invention can be used in various cosmetic, pharmaceutical and therapeutic designs, devices and applications.

The Use of Glycylated Sugar Alcohols for Preventing RNA Degradation.

Small non-coding RNAs (ncRNA) are known to be extremely unstable and degradable in vitro and particularly in vivo. The degradation of these ncRNA structures can be measured by high performance liquid chromatography (HPLC) analysis (Example 4) in normal saline (0.9% w/v NaCl), wherein normal saline is used to mimic human body fluids in vivo. For example, as a result shown in FIG. 2A, after comparing fresh and 3-day-old miR-302 precursor samples (Example 1) dissolved in autoclaved normal saline and then store at room temperature, we found that over 69% of pre-miR-302 (mostly 1-hairpin precursors) and pri-miR-302 (4-hairpin cluster) were quickly degraded within three days, which is too short to elicit any RNA interference (RNAi)-associated gene silencing effect. Pri-miR-302, the primary RNA transcript of the miR-302 familial cluster gene (FIG. 2B; SEQ.ID.NO.1), can be processed into one or more pre-miRNA (i.e. pre-miR-302) molecules by Drosha/Pasha digestion (to form exonic pre-miRNA), spliceosomal splicing/excision (to form intronic pre-miRNA), or hydrolysis. Pre-miR-302 is the functional form of miR-302 precursor that can be further processed by RNase III Dicer and assembled into an RNA-induced silencing complex (RISC) for eliciting its specific gene silencing effects. As shown in FIG. 2C, we have identified that the processed pre-miR-302 isoforms include pre-miR-302a (SEQ.ID.NO.2), pre-miR-302b (SEQ.ID.NO.3), pre-miR-302c (SEQ.ID.NO.4), and pre-miR-302d (SEQ.ID.NO.5). Yet, due to their fast degradation, these pre-miR-302 molecules can be clearly identified in fresh but barely from 3-day-old samples with microRNA sequencing.

In order to preserve fresh miRNA structures, we added and mixed 0.1 M glycylated sugar alcohols (i.e. MGG/DGG/TGG) into fresh miRNA miR-302 samples and then performed the same experimental procedures and HPLC analyses as aforementioned. The final concentration of glycylated sugar alcohol solution used to dissolve RNA/DNA can be ranged from about 0.1 µM to about 10 M, most preferably about 0.05 M to 1.5 M. The maximal solubility of RNA/DNA in MGG/DGG/TGG solution is up to 12~15 mg/mL. As shown in FIG. 2D, we found almost no degradation in these sugar-alcohol-treated samples three days later in normal saline at room temperature. This result has clearly indicated that glycylated sugar alcohols can preserve the integrity of hairpin-like RNA structures and hence prevent the degradation of these hairpin RNAs, such as microRNA precursors (miRNA), small hairpin RNAs (shRNA), short interfering RNAs (siRNA), and ribozymes. Given that RNAi-associated gene silencing effects require at least a three-day period of activation time to be fully effective, the novel sugar alcohol composition found in the present invention is surely useful for stabilizing the structures of these hairpin RNAs long enough to elicit their specific gene silencing effects. Thus, the present invention can be applied to preserve both the structural integrity and functional efficacy of these functional hairpin RNAs in a variety of cosmedical, pharmaceutical and therapeutic products as well as applications.

Identification of Sugar Alcohol-delivered MicroRNAs in Transfected Cells.

For measuring the deliver efficiency of sugar alcohol-treated nuclei acid compositions into mammalian cells, we isolated and purified miR-302 precursors (i.e. pri- and pre-miR-302s) from competent cells transfected with the miR-302 familial cluster gene (Example 1) and then tried to deliver 400 µg of the isolated miR-302 precursors with 1.0 M DGG/TGG into approximately 2-4 million human keratinocytes grown in 2 ml cell culture medium (Example 3). To increase delivery efficiency, concentrated DGG/TGG was further purified from the mixture solution of MGG/DGG/TGG using HPLC (FIG. 8). As shown in FIGS. 3A and 3B, microarray results (Example 5) revealed that these isolated miR-302 precursors were successfully delivered into the target cells and further processed into mature miR-302 molecules (e.g. miR-302a, b, c, d and miR-302a*, b*, c*, d*), indicating that glycylated sugar alcohols not only can efficiently deliver these hairpin RNAs into human cells but also facilitate their assembly into RISCs for eliciting their desired functions. Also, since keratinocytes do not express any miR-302 (FIG. 3A), the highly abundant miR-302 molecules found in the treated keratinocytes (FIG. 3B) must all result from the delivery effect of glycylated sugar alcohols and the delivered miR-302 precursors thereof, suggesting that this highly efficient delivery effect is likely facilitated by an active transporting mechanism such as endocytosis. In nature, such modified sugar alcohols and their derivatives may be absorbed by cells via a receptor-mediated endocytosis mechanism.

Effects of Sugar Alcohol-delivered Anti-Cancer MicroRNAs against Cancer Cell Growth.

To further observe the sugar alcohol-delivered drug effects, we treated human hepatocellular carcinoma HepG2 cells with MGG/DGG/TGG-encapsulated miR-302 precursors (pri-/pre-miR-302s) using three different final concentrations 0, 200, and 400 µg/ml, respectively. Also, in order to concurrently demonstrate the parallel effects of MGG/DGG/TGG-mediated miR-302 delivery, we encapsulated these pri-/pre-miR-302s with sugar alcohols modified by four different levels of glycylation, including 0, 75, 750, and 1500 mg/10 mL glycine-glycylated glycerol (MGG/DGG/TGG), respectively. Our previous in-vitro studies using vector-based expression have shown that miR-302 can function to inhibit over 95% cancer cell proliferation while only affecting less than 5% to 10% normal cell growth (Lin et al., (2010) Cancer Research 70:9473-9482). As shown in FIG. 4A, the present studies using glycylated sugar alcohol-encapsulated miR-302 delivery showed a similar dose-dependent inhibitory effect on human cancer cell growth, whereas FIG. 4B further shows that the use of glycylated sugar alcohols alone at an equal volume (the equal volume of the same control volume, 35 µl or 70 µl) did not result in any effect or cytotoxicity, indicating that the observed therapy effect of miR-302 is indeed delivered by glycylated sugar alcohols after encapsulating formulation (Example 2).

The same MGG/DGG/TGG-delivered tumor suppression effects of miR-302 have been observed in vivo. As shown in FIG. 4C, we injected 250 µg of MGG/DGG/TGG-encapsulated pri-/pre-miR-302s (in 5 µg/µL concentration) into each human Huh-7 liver cancer xenograpft implanted on NOD SCID nude mice (n=6 for each group). After nine treatments (2-4 day interval between two treatments), the therapeutic results showed a significant >73% reduction in the sizes of all treated human cancer xenografts compared to those control xenografts without any treatment. Most notably, while the control cancers grew over 11 folds in size during the three-week experiment time, the treated group only expanded 3 folds, indicating a very beneficial tumor suppression effect for treating fast proliferating cancers and preventing cancer relapse after surgical removal. Hence, the results of FIG. 4C clearly demonstrate the high efficiency of glycylated sugar/sugar alcohol-mediated miRNA/shRNA/siRNA delivery in vivo. Since tumor/cancer cells absorb sugar-like materials much more quickly than normal cells, the glycylated sugar/sugar alcohol-encapsulated miRNAs/shRNAs/siRNAs can be easily uptake by tumors/cancers in vivo. It is also noted that these glycylated sugars/sugar alcohols not only deliver the encapsulated RNAs but also successfully introduce the delivered RNA functions into targeted cells.

In Vivo Distribution of Sugar Alcohol-Delivered miRNA/siRNA Mimics in Mouse.

To test the in-vivo deliver efficiency and toxicity of sugar alcohol-encapsulated nucleic acid compositions, we injected 200 µg of synthetic miR-302 mimics (i.e. siR-302 from Example 1) dissolved in 200 µl of 1.0 M DGG/TGG into each of C57BL/6J strain mice via tail vein injection (Example 6; n=6). After 24-hour incubation, we kept 4 mice for further survival rate analysis and sacrificed two for studying the DGG/TGG-delivered siR-302 distribution in vivo. Since the siR-302 molecules were all labeled with infra-red fluorescent dye Cy5.5, we could detect their in-vivo tissue distribution using a bio-imaging system or directly observe their fluorescent signals in mouse tissue sections under a fluorescent microscope. As shown in FIG. 5, after microscopic examination of various tissue/organ sections collected from the injected mice, we found that the majority of Cy5.5-labeled siRNA molecules were delivered into heart, liver, spleen and blood vessel endothelial cells as well as sporadically detected in bone marrow and lung cells, confirming the delivery efficiency of glycylated sugar/sugar alcohol-encapsulated nucleic acid compositions in vivo. On the other hand, the other 4 mice with the same sugar-alcohol-encapsulated siR-302 injection showed no adverse effect during the whole two-week experiment time (FIG. 6), further revealing the in-vivo safety of this novel delivery composition and method.

In sum, we have practically enabled the utilization of a novel sugar alcohol composition not only for preserving the structural integrity of nucleic acid compositions but also for delivering these functional nucleic acid compositions into cells in vitro and in vivo. These functional nucleic acid compositions may include, but not limited, microRNA precursors (miRNA), small hairpin RNAs (shRNA), short interfering RNAs (siRNA), ribozymes, antisense RNAs/DNAs, RNA-DNA hybrids and DNA vectors/vaccines. As safety and efficacy are the two major concerns during drug delivery, the non-toxic and highly tissue-penetrating feature of the presently invented sugar alcohol compositions can overcome these concerns and satisfy the needs of efficient in-vivo delivery for a variety of nucleic acid-based cosmetic, pharmaceutical and therapeutic applications. In particular, it is noted that all materials used to produce these modified (glycylated) sugar alcohol compositions are non-toxic under Food and Drug Administration (FDA) regulations.

A. Definitions

To facilitate understanding of the invention, a number of terms are defined below:

Nucleotide: a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. A nucleoside containing at least one phosphate group bonded to the 3' or 5' position of the pentose is a nucleotide. DNA and RNA are consisted of different types of nucleotide units called deoxyribonucleotide and ribonucleotide, respectively.

Oligonucleotide: a molecule comprised of two or more DNAs and/or RNAs, preferably more than three, and usually more than ten. An oligonucleotide longer than 13 nucleotide monomers is also called polynucleotiude. The exact size will depend on many factors, which in turn depends on the ultimate function or use of the oligonucleotide. The oligonucleotide may be generated in any manner, including chemical synthesis, DNA replication, RNA transcription, reverse transcription, or a combination thereof.

Nucleotide Analog: a purine or pyrimidine nucleotide that differs structurally from adenine (A), thymine (T), guanine (G), cytosine (C), or uracil (U), but is sufficiently similar to substitute for the normal nucleotide in a nucleic acid molecule.

Nucleic Acid Composition: a nucleic acid composition refers to a natural or synthetic oligonucleotide or polynucleotide, such as a DNA or RNA sequence, or a mixed DNA/RNA hybrid sequence, in either a single-stranded or a double-stranded molecular structure.

Gene: a nucleic acid composition whose oligonucleotide or polynucleotide sequence codes for an RNA and/or a polypeptide (protein). A gene can be either RNA or DNA. A gene may encode a non-coding RNA, such as small hairpin RNA (shRNA), microRNA (miRNA), rRNA, tRNA, snoRNA, snRNA, and their RNA precursors as well as derivatives. Alternatively, a gene may encode a protein-coding RNA essential for protein/peptide synthesis, such as messenger RNA (mRNA) and its RNA precursors as well as derivatives. In some cases, a gene may encode a protein-coding RNA that also contains at least a microRNA or shRNA sequence.

Primary RNA Transcript: an RNA sequence that is directly transcribed from a genetic DNA without any RNA processing or modification, which may be selected from the group consisting of hnRNA, pre-mRNA, rRNA, tRNA, snoRNA, snRNA, pri-microRNA (pri-miRNA), viral RNA and their RNA precursors as well as derivatives. After transcription, uracil (U) is substituted for thymine (T).

Precursor messenger RNA (pre-mRNA): primary messenger RNA transcripts of a protein-coding gene, which are produced by eukaryotic type-II RNA polymerase (Pol-II) machineries in eukaryotes through an intracellular mechanism termed transcription. A pre-mRNA sequence contains a 5'-untranslated region (UTR), a 3'-UTR, exons and introns.

Messenger RNA (mRNA): assembly of pre-mRNA exons, which is formed after intron removal by intracellular RNA splicing machineries (spliceosomes) and served as a protein-coding RNA for peptide/protein synthesis. The peptides/proteins encoded by mRNAs include, but not limited, enzymes, growth factors, insulin, antibodies and their analogs/homologs as well as derivatives.

Complementary DNA (cDNA): a single-stranded or double-stranded DNA that contains a sequence complementary to an mRNA sequence and does not contain any intronic sequence.

Sense: a nucleic acid molecule in the same sequence order and composition as the homologous mRNA. The sense conformation is indicated with a "+", "s" or "sense" symbol.

Antisense: a nucleic acid molecule complementary to the respective mRNA molecule. The antisense conformation is indicated as a "−" or "*" symbol or with an "a" or "antisense" in front of the DNA or RNA, e.g., "aDNA" or "aRNA".

Base Pair (bp): a partnership of adenine (A) with thymine (T), or of cytosine (C) with guanine (G) in a double stranded DNA molecule. In RNA, uracil (U) is substituted for thymine. Generally the partnership is achieved through hydrogen bonding. For example, a sense nucleotide sequence "5'-A-T-C-G-U-3'" can form complete base pairing with its antisense sequence "5'-A-C-G-A-T-3'".

5'-end: a terminus lacking a nucleotide at the 5' position of successive nucleotides in which the 5'-hydroxyl group of one nucleotide is joined to the 3'-hydroyl group of the next nucleotide by a phosphodiester linkage. Other groups, such as one or more phosphates, may be present on the terminus.

3'-end: a terminus lacking a nucleotide at the 3' position of successive nucleotides in which the 5'-hydroxyl group of one nucleotide is joined to the 3'-hydroyl group of the next nucleotide by a phosphodiester linkage. Other groups, most often a hydroxyl group, may be present on the terminus.

Template: a nucleic acid molecule being copied by a nucleic acid polymerase. A template can be single-stranded, double-stranded or partially double-stranded, depending on the polymerase. The synthesized copy is complementary to the template, or to at least one strand of a double-stranded or partially double-stranded template. Both RNA and DNA are synthesized in the 5' to 3' direction. The two strands of a nucleic acid duplex are always aligned so that the 5' ends of the two strands are at opposite ends of the duplex (and, by necessity, so then are the 3' ends).

Nucleic Acid Template: a double-stranded DNA molecule, double stranded RNA molecule, hybrid molecules such as DNA-RNA or RNA-DNA hybrid, or single-stranded DNA or RNA molecule.

Conserved: a nucleotide sequence is conserved with respect to a pre-selected (referenced) sequence if it non-randomly hybridizes to an exact complement of the pre-selected sequence.

Homologous or Homology: a term indicating the similarity between a polynucleotide and a gene or mRNA sequence. A nucleic acid sequence may be partially or completely homologous to a particular gene or mRNA sequence, for example. Homology may be expressed as a percentage determined by the number of similar nucleotides over the total number of nucleotides.

Complementary or Complementarity or Complementation: a term used in reference to matched base pairing between two polynucleotides (i.e. sequences of an mRNA and a cDNA) related by the aforementioned "base pair (bp)" rules. For example, the sequence "5'-A-G-T-3" is complementary to the sequence "5'-A-C-T-3'", and also to "5'-A-C-U-3'". Complementation can be between two DNA strands, a DNA and an RNA strand, or between two RNA strands. Complementarity may be "partial (imperfect)" or "complete (perfect)" or "total". Partial complementarity or complementation occurs when only some of the nucleic acid bases are matched according to the base pairing rules. Complete or total complementarity or complementation occurs when the bases are completely or perfectly matched between the nucleic acid strands. The degree of complementarity between nucleic acid strands has significant effects on the efficiency and strength of hybridization between nucleic acid strands. This is of particular importance in amplification reactions, as well as in detection methods that depend on binding between nucleic acids. Percent complementarity or complementation refers to the number of mismatch bases over the total bases in one strand of the nucleic acid. Thus, a 50% complementation means that half of the bases were mismatched and half were matched. Two strands of nucleic acid can be complementary even though the two strands differ in the number of bases. In this situation, the complementation occurs between the portion of the longer strand corresponding to the bases on that strand that pair with the bases on the shorter strand.

Complementary Bases: nucleotides that normally pair up when DNA or RNA adopts a double stranded configuration.

Complementary Nucleotide Sequence: a sequence of nucleotides in a single-stranded molecule of DNA or RNA that is sufficiently complementary to that on another single strand to specifically hybridize between the two strands with consequent hydrogen bonding.

Hybridize and Hybridization: the formation of duplexes between nucleotide sequences which are sufficiently complementary to form complexes via base pairing. Where a primer (or splice template) "hybridizes" with target (template), such complexes (or hybrids) are sufficiently stable to serve the priming function required by a DNA polymerase to initiate DNA synthesis. There is a specific, i.e. non-random, interaction between two complementary polynucleotides that can be competitively inhibited.

Posttranscriptional Gene Silencing: a targeted gene knock-out or knockdown effect at the level of mRNA degradation or translational suppression, which is usually triggered by either foreign/viral DNA or RNA transgenes or small inhibitory RNAs.

RNA Interference (RNAi): a posttranscriptional gene silencing mechanism in eukaryotes, which can be triggered by small inhibitory RNA molecules such as microRNA (miRNA), small hairpin RNA (shRNA) and small interfering RNA (siRNA). These small RNA molecules usually function as gene silencers, interfering with either expression of intracellular genes or translation of the gene transcripts, or both, that contain certain target sequences either completely or partially complementarity to the small RNAs.

Gene Silencing Effect: a cell response after a gene function is suppressed, consisting of, but not limited, inhibition of oncogene expression, inhibition of cell proliferation, cell cycle arrest, tumor suppression, cancer regression, cancer prevention, cell apoptosis, cell repairing and/or rejuvenation, cell reprogramming, reprogramming diseased cells to a relatively normal state (spontaneous healing), and a combination thereof.

Non-coding RNA: an RNA transcript that cannot be used to synthesize peptides or proteins through intracellular translation machineries. Non-coding RNA includes long and short regulatory RNA molecules such as microRNA (miRNA), small hairpin RNA (shRNA), small interfering RNA (siRNA) and double strand RNA (dsRNA). These regulatory RNA molecules usually function as gene silencers, interfering with expression of intracellular genes containing either completely or partially complementarity to the non-coding RNAs.

MicroRNA (miRNA): single-stranded RNA capable of binding to targeted gene transcripts (mRNAs) that have partial complementarity to the sequence of microRNA. Mature microRNA is usually sized about 17-27 oligonucleotides in length and is able to either directly degrade its intracellular mRNA target(s) or suppress the protein translation of its targeted mRNA(s), depending on the complementarity between the microRNA and its target mRNA(s). Native microRNAs are found in almost all eukaryotes, functioning as a defense against viral infections and allowing regulation of specific gene expression during development of plants and animals. In principle, one microRNA often target multiple target mRNAs to fulfill its full functionality while on the other hand multiple miRNAs may target the same gene transcripts to enhance the effect of gene silencing.

MicroRNA Precursor (pri-/pre-miRNA): hairpin-like single-stranded RNA containing stem-arm and stem-loop regions for interacting with RNase III Dicer endoribonucleases to produce one or multiple mature microRNAs (miRNAs) capable of silencing a targeted gene or a specific group of targeted genes that contain full or partial complementarity to the mature microRNA sequence(s). The stem-arm of a pri-/pre-miRNA can form either a perfectly (100%) or a partially (mis-matched) hybrid duplexes, while the stem-loop connects one end of the stem-arm duplex to form a circle or hairpin-loop conformation required for being assembled into an RNA-induced silencing complex (RISC) with some argonaute proteins (AGO).

Small interfering RNA (siRNA): short double-stranded RNA sized about 18-27 perfectly base-paired ribonucleotide duplexes and capable of degrading target gene transcripts with almost perfect complementarity.

Small or short hairpin RNA (shRNA): single-stranded RNA that contains a pair of partially or completely matched stem-arm nucleotide sequences divided by an unmatched loop oligonucleotide to form a hairpin-like structure. Many natural miRNAs are derived from hairpin-like RNA precursors, namely precursor microRNA (pre-miRNA).

Vector: a recombinant nucleic acid composition such as recombinant DNA (rDNA) capable of movement and residence in different genetic environments. Generally, another nucleic acid is operatively linked therein. The vector can be capable of autonomous replication in a cell in which case the vector and the attached segment is replicated. One type of preferred vector is an episome, i.e., a nucleic acid molecule capable of extrachromosomal replication. Preferred vectors are those capable of autonomous replication and expression of nucleic acids. Vectors capable of directing the expression of genes encoding for one or more polypeptides and/or non-coding RNAs are referred to herein as "expression vectors" or "expression-competent vectors". Particularly important vectors allow cloning of cDNA from mRNAs produced using a reverse transcriptase. A vector may contain components consisting of a viral or a type-II RNA polymerase (Pol-II or pol-2) promoter, or both, a Kozak consensus translation initiation site, polyadenylation signals, a plurality of restriction/cloning sites, a pUC origin of replication, a SV40 early promoter for expressing at least an antibiotic resistance gene in replication-competent prokaryotic cells, an optional SV40 origin for replication in mammalian cells, and/or a tetracycline responsive element. The structure of a vector can be a linear or circular form of single- or double-stranded DNA selected form the group consisting of plasmid, viral vector, transposon, retrotransposon, DNA transgene, jumping gene, and a combination thereof.

Promoter: a nucleic acid to which a polymerase molecule recognizes, or perhaps binds to, and initiates RNA transcription. For the purposes of the instant invention, a promoter can be a known polymerase or its cofactor binding site, an enhancer and the like, any sequence that can initiate synthesis of RNA transcripts by a desired polymerase.

RNA Processing: a cellular mechanism responsible for RNA maturation, modification and degradation, including RNA splicing, intron excision, exosome digestion, nonsense-mediated decay (NMD), RNA editing, RNA processing, and a combination thereof.

Targeted Cell: a single or a plurality of human cells selected from the group consisting of a somatic cell, a tissue, a stem cell, a germ-line cell, a teratoma cell, a tumor cell, a cancer cell, and a combination thereof.

Cancerous Tissue: a neoplastic tissue derived from the group consisting of skin cancer, prostate cancer, breast cancer, liver cancer, lung cancer, brain tumor/cancer, lymphoma, leukemia and a combination thereof.

Gene Delivery: a genetic engineering method selected from the group consisting of polysomal transfection, liposomal transfection, chemical transfection, electroporation, viral infection, DNA recombination, transposon insertion, jumping gene insertion, microinjection, gene-gun penetration, and a combination thereof.

Genetic Engineering: a DNA recombination method selected from the group consisting of DNA restriction and ligation, homologous recombination, transgene incorporation, transposon insertion, jumping gene integration, retroviral infection, and a combination thereof.

Tumor Suppression Effect: a cellular anti-tumor and/or anti-cancer mechanism and response consisting of, but not limited, cell cycle attenuation, cell cycle arrest, inhibition of tumor cell growth, inhibition of cell tumorigenecity, inhibition of tumor/cancer cell transformation, induction of tumor/cancer cell apoptosis, induction of normal cell recovery, reprogramming high-grade malignant cancer cells to a more benign low-grade state (tumor regression), and a combination thereof.

Cancer Therapy Effect: a cell response and/or cellular mechanism resulted from a drug treatment, including, but not limited, inhibition of oncogene expression, inhibition of cancer cell proliferation, inhibition of cancer cell invasion and/or migration, inhibition of cancer metastasis, induction of cancer cell death, prevention of tumor/cancer formation, prevention of cancer relapse, suppression of cancer progression, repairing damaged tissue cells, reprogramming high-grade malignant cancers to a more benign low-grade state (cancer regression/remission), and a combination thereof.

Cancer Reversion: a reprogramming mechanism that resets the malignant properties of high-grade cancers back to a relatively normal-like low-grade state in vitro, ex vivo or in vivo.

Targeted Cell: a single or a plurality of human cells selected from the group consisting of a somatic cell, a tissue, a stem cell, a germ-line cell, a teratoma cell, a tumor cell, a cancer cell, and a combination thereof.

Glycylation: a chemical reaction that replaces the hydroxyl (HO—) groups of a sugar alcohol or sugar with glycine's or glycylated amino acid's glycyl ($NH_2CH_2COO$—) groups and thus results in the formation of an ether (R—O—R) linkage between each OH-removed carbon of the sugar alcohol/sugar and the glycyl group of the glycine and/or glycylated amino acid.

Pharmaceutical and Therapeutic Application: a biomedical utilization, treatment method, device and/or apparatus useful for diagnosis, stem cell generation, stem cell research and/or therapy development, tissue/organ repair and/or rejuvenation, wound healing treatment, tumor suppression, cancer therapy and/or prevention, disease treatment, drug production, and a combination thereof.

Prokaryotes: a one-cell, organism that lacks a distinct membrane-bound nucleus and has its genetic materials in the form of a continuous strand of DNA.

B. Compositions and Applications

A composition and its use for formulating nucleic acid compositions with sugar alcohols into delivery complexes for both in-vitro and in-vivo delivery into mammalian cells, comprising: (a) at least a nucleic acid composition with at least a negative charge, and (b) at least a sugar alcohol or sugar modified by glycylation; wherein (a) and (b) are mixed together under a condition to form delivery complexes. The nucleic acid composition can be microRNA precursors (miRNA), small hairpin RNAs (shRNA), short interfering RNAs (siRNA), ribozymes, antisense RNAs/DNAs, RNA-DNA hybrids, DNA vectors/vaccines, and a combination thereof. The condition required for the delivery complex formation is below pH8.0, of which the pH value is preferred to be about pH2.5 to about pH7.0.

In principle, the present invention teaches a novel method of glycylation and its use for generating positively charged sugar alcohol and/or sugar compounds capable of interacting with negatively charged nucleic acid compositions via ionic binding and/or electrostatic affinity rather than covalent conjugation or hydrogen bonding (FIG. 7). Since such ionic/electrostatic affinity is formed between the glycyl groups of the modified sugars/sugar alcohols and the phosphodiester-linked backbones of RNAs/DNAs, the attached sugars/sugar alcohols can then repel water molecules away from the RNA/DNA backbones, so as to prevent hydrolysis and thus protect the intact structures of these nucleic acid compositions for better delivery of their drug effects into cells in vivo as well as in vitro.

In addition, the present invention discovered for the first time that chemical compounds containing sugar alcohols and/or sugars can protect the integrity of nucleic acid compositions, such as miRNA, shRNA, siRNA, ribozyme and DNA, from degradation. Hence, the present invention is not only a composition and its use for delivering nucleic acid-based drugs/vaccines into cells but also a material formula for preserving the structural integrity and functional efficacy of these nucleic acid-based drugs and/or vaccines in vivo as well as in vitro. Due to these novel features, the present invention is very useful for developing and/or improving a variety of nucleic acid-based cosmetic, pharmaceutical and therapeutic applications.

BRIEF DESCRIPTION OF THE DRAWINGS

The patent or application file contains at least one color drawing. Copies of this patent or patent application publication with color drawing will be provided by the USPTO upon request and payment of the necessary fee.

Referring particularly to the drawings for the purpose of illustration only and not limitation, there is illustrated:

FIGS. 2A-2D show the results of high performance liquid chromatography (HPLC) analyses before and after degradation of miR-302 precursors (i.e. pri- and pre-miR-302). FIG. 2A shows the comparison of HPLC patterns between fresh and degraded miR-302 precursors. The result of fresh sample (2A top) consists of total four peaks as follows: a small peak at 4.25 min (single nucleotide), a major peak at 9.50 min (1-hairpin pre-miR-302s), another small peak at 10.4 min (2-hairpin pre-miR-302s), and another major peak at 12.5 min (4-hairpin cluster pri-miRNA), whereas degraded sample (stored in normal saline for 3 days) displays a very smeared pattern (2A bottom). FIG. 2B shows the sequence of the miR-302 familial cluster gene from where the miR-302 precursors are transcribed and processed. FIG. 2C shows the individual sequences of 1-hairpin pre-miR-302 isoforms, including pre-miR-302a (SEQ.ID.NO.2), pre-miR-302b (SEQ.ID.NO.3), pre-miR-302c (SEQ.ID.NO.4), and pre-miR-302d (SEQ.ID.NO.5). FIG. 2D shows the comparison of HPLC patterns between fresh and sugar alcohol-protected miR-302 precursors, showing no degradation after 3-day storage in normal saline.

FIG. 3A shows no miR-302 expression in blank keratinocytes, whereas FIG. 3B demonstrates that abundant miR-302 molecules were detected after sugar alcohol-mediated miR-302-transfection, indicating the success of sugar alcohol-based small RNA delivery into human cells.

FIGS. 4A-4C show the therapeutic effects of sugar alcohol-mediated anti-cancer drug (i.e. miR-302) delivery. Three different final concentrations of isolated miR-302 precursors (pri-/pre-miR-302s) at 0 (control), 200, and 400 µg/ml, respectively, were used to treat human liver cancer HepG2 cells. Also, in order to demonstrate the delivery efficiency of sugar alcohols after modification, we encapsulated these pri-/pre-miR-302s with sugar alcohols modified by four different levels of glycylation, including glycerin glycylated with 0 (control), 75, 750 and 1500 mg of glycine (Gly), respectively, which consequently result in a final MGG/DGG/TGG concentration of 0, ~0.1, ~0.5 and ~1.0 M, respectively. As a result, FIG. 4A shows a significant dose-dependent increase of the miR-302-induced tumor suppression effects on human cancer cell growth following the increase of glycylated levels of MGG/DGG/TGG delivery (=Formulation 5). Meanwhile, FIG. 4B shows the treatments of MGG/DGG/TGG alone without miR-302 did not result in any effect or cytotoxicity. To further evaluate glycylated sugar/sugar alcohol-delivered miR-302 effects in vivo, FIG. 4C shows the therapeutic results of MGG/DGG/TGG-encapsulated pri-/pre-miR-302 treatments, resulting in an average >71% reduction in the sizes of human Huh-7 cancer xenografts grown on NOD SCID nude mice (n=6).

EXAMPLES

In the experimental disclosure which follows, the following abbreviations apply: M (molar); mM (millimolar); μm (micromolar); mol (moles); pmol (picomoles); gm (grams); mg (milligrams); μg (micrograms); ng (nanograms); L (liters); ml (milliliters); μl (microliters); ° C. (degrees Centigrade); RNA (ribonucleic acid); DNA (deoxyribonucleic acid); dNTP (deoxyribonucleotide triphosphate); PBS (phosphate buffered saline); NaCl (sodium chloride); HEPES (N-2-hydroxyethylpiperazine-N-2-ethanesulfonic acid); HBS (HEPES buffered saline); SDS (sodium dodecylsulfate); Tris-HCl (tris-hydroxymethylaminomethane-hydrochloride); ATCC (American Type Culture Collection, Rockville, Md.); hESC (human embryonic stem cells); and iPSC (induced pluripotent stem cells).

1. MicroRNA (miRNA) Production and Isolation and siRNA Synthesis

Dicer-negative cells were acquired from Zymo Research (Irvine, Calif.), transduced with a pre-made miR-302 expression lentiviral vector pLenti-EF1alpha-RGFP-miR302 (Mello Biotech, Santa Fe Springs, Calif.), and maintained according to manufacturers' suggestions. MicroRNAs were isolated with a mirVana™ miRNA isolation kit (Ambion, Austin, Tex.), following the manufacturer's protocol. The isolated RNAs (pri-/pre-miR-302) were dissolved in autoclaved 1× TE buffer and stored at −80° C. till use. For stability tests with HPLC, a desired amount of the isolated RNAs was re-collected with an Amicon Ultra-0.5 mL 30K filter column (Millipore, Billerica, Mass.) and re-dissolved in autoclaved normal saline. For siR-302 preparation, synthetic miR-302 mimics were purchased from Sigma-Genosys (St. Louis, Mo.), containing two cyanine 5.5 (Cy5.5)-labeled RNA sequences: 5'-Cy5.5-UAAGUGCUUC CAUGUUUUAG UGU-3' (SEQ.ID.NO.6) and 5'-Cy5.5-ACACUAAAAC AUGGAAGCAC UUA-3' (SEQ.ID.NO.7). In experiments, siR-302 was formed by the hybrids of SEQ.ID.NO.6 and SEQ.ID.NO.7.

2. Glycylation of Sugar Alcohols and Formulation of miRNA/shRNA/siRNA

Figure 1A:
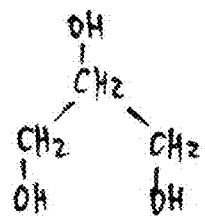
FIGS. 1A and 1B show the chemical reaction of glycylation and the resulting glycylated sugar alcohols thereof. For example, when glycerol (glycerin) is used as a model of sugar alcohol, two major reactive products for nucleic acid delivery can be identified: one is 1,3-diglycylglycerol (1A; DGG) and the other is 1,2,3-triglycylglyceride (1B; TGG). DGG is a partially glycylated product (1A), while TGG is a completely (or fully) glycylated product (1B).
Figure 1A:
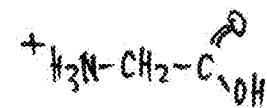
Figure 1A:
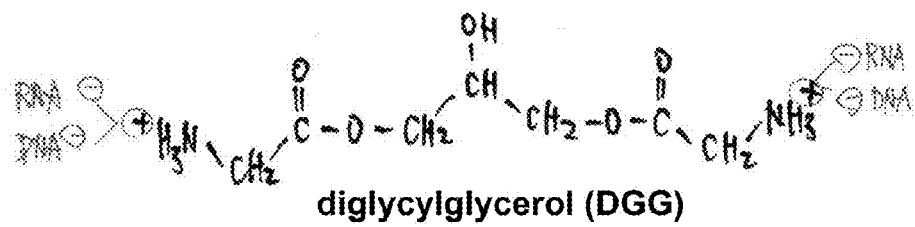
Figure 1B:
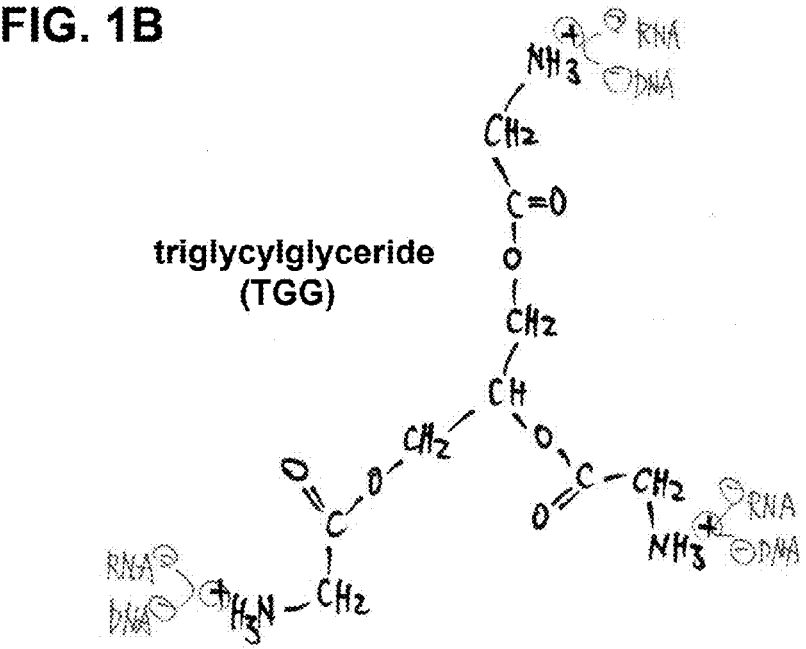
Figure 7:
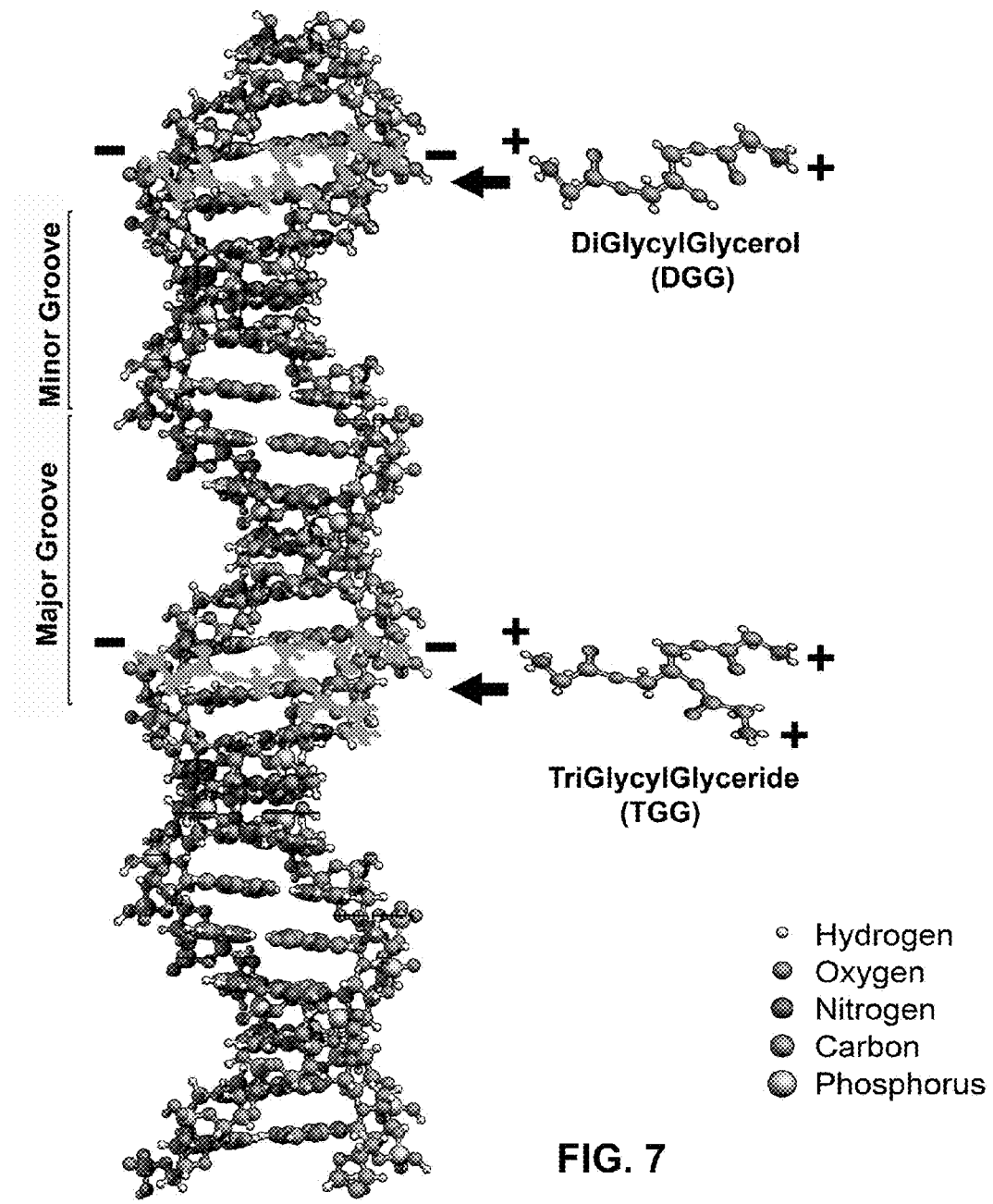
FIG. 7 illustrates the interaction of electrostatic affinity between siRNA/shRNA/miRNA/microRNA precursor/ribozyme/DNA and glycylated sugars/sugar alcohols (for example, DGG and TGG). The interaction area is labeled by green shadows to indicate the binding of DGG/TGG to the phosphate groups of RNA/DNA backbones. The phosphate groups of RNA/DNA are resided in the minor grooves of a nucleic acid strand. After multiple glycylated sugars/sugar alcohols attach to the RNA/DNA strands, it forms a sugar/sugar alcohol coating on the encapsulated RNA/DNA, so as to protect the RNA/DNA structures and facilitate their delivery in vitro and in vivo.

Although the natural way of sugar/sugar alcohol glycylation is unclear, we have developed a chemical procedure to artificially make glycylated sugar alcohols and sugars. First, a pre-made base solution was prepared, containing 1.0 M glycerol, 0.3 M fructose, and 0.9% (w/v) NaCl at about pH 2.5~pH 8.0, depending on the source of sugar alcohol(s) used. We have noted that any sugar alcohol contaminated with alkaline materials might not work for glycylation. For activating glycylation, about a final concentration of 0.05~3.0 M glycine was added, depending on the desired concentration of final glycylated sugar alcohols/sugars, into the pre-made base solution and mixed well. Then, the glycine-added solution was kept strictly under a neutral to slightly acidic condition and incubated at a temperature over 45° C., preferably 75° C.~175° C., for >30 min, preferably about 12~24 hours. Optionally, after that, 0.1 M mannitol was added to absorb any excessive glycine and the solution was further incubated over 45° C. for another 12~24 hours. When the final solution pH reached about 6.0 to 7.0, the glycylation of sugar alcohols/sugars was completed and this final solution was ready to be used for formulating and delivering negatively charged materials. The formulation is simply done by mixing the glycylated sugars/sugar alcohols with desired nucleic acid compositions. After that, the electrostatic/charge affinity between the glycylated sugar alcohols/sugars and nucleic acid compositions will form encapsulated delivery complexes (FIG. 7), which can then be absorbed by cells through active endocytosis. For demonstration, a schematic glycylation reaction using glycerol as an example was shown in FIGS. 1A and 1B.

3. Human Cell Culture and Transfection

Human keratinocytes was purchased from Invitrogen and cultivated in EpiLife serum-free cell culture medium supplemented with human keratinocyte growth supplements (HKGS, Invitrogen, Carlsbad, Calif.) in the absence of antibiotics at 37° C. under 5% $CO_2$. Cells were passaged at about 50%-70% confluence by exposing the cells to trypsin/EDTA for about 1 min and then rinsing two times in HBSS containing trypsin inhibitor. The detached cells were replated at 1:5 dilution in fresh EpiLife medium with HKGS supplements. On the other hand, human liver cancer cell line HepG2 was obtained from ATCC and maintained according to manufacturer's suggestions. For miRNA transfection, pri-/pre-miR-302 prepared from Example 1 was dissolved in 0.1~1.0 M of MGG/DGG/TGG solution at a desired concentration up to 5~10 mg/mL and then directly applied to cell culture medium based on the miRNA amount needed. For example, to deliver 200 μg pri-/pre-miR-302, we would need to add 40 μl of the MGG/DGG/TGG-dissolved pri-/pre-miR-302 (at 5 mg/ml) into the cell culture medium and then mix well with the cells. Since MGG/DGG/TGG is extremely safe and non-toxic, the tested cells could be cultivated in 0.1 M MGG/DGG/TGG with all necessary supplements and still not showing any adverse effect up to 48 hours. As a result, for cells growing in a 2-ml culture dish, the maximal transfection amount of miRNA/shRNA/siRNA with 0.1 M MGG/DGG/TGG is estimated to be about 10 mg, indicating a highly efficient delivery level that none of the previously reported liposomal and sugar-based delivery agents can achieve.

4. High Performance Liquid Chromatography (HPLC) Analysis

Figure 2A:
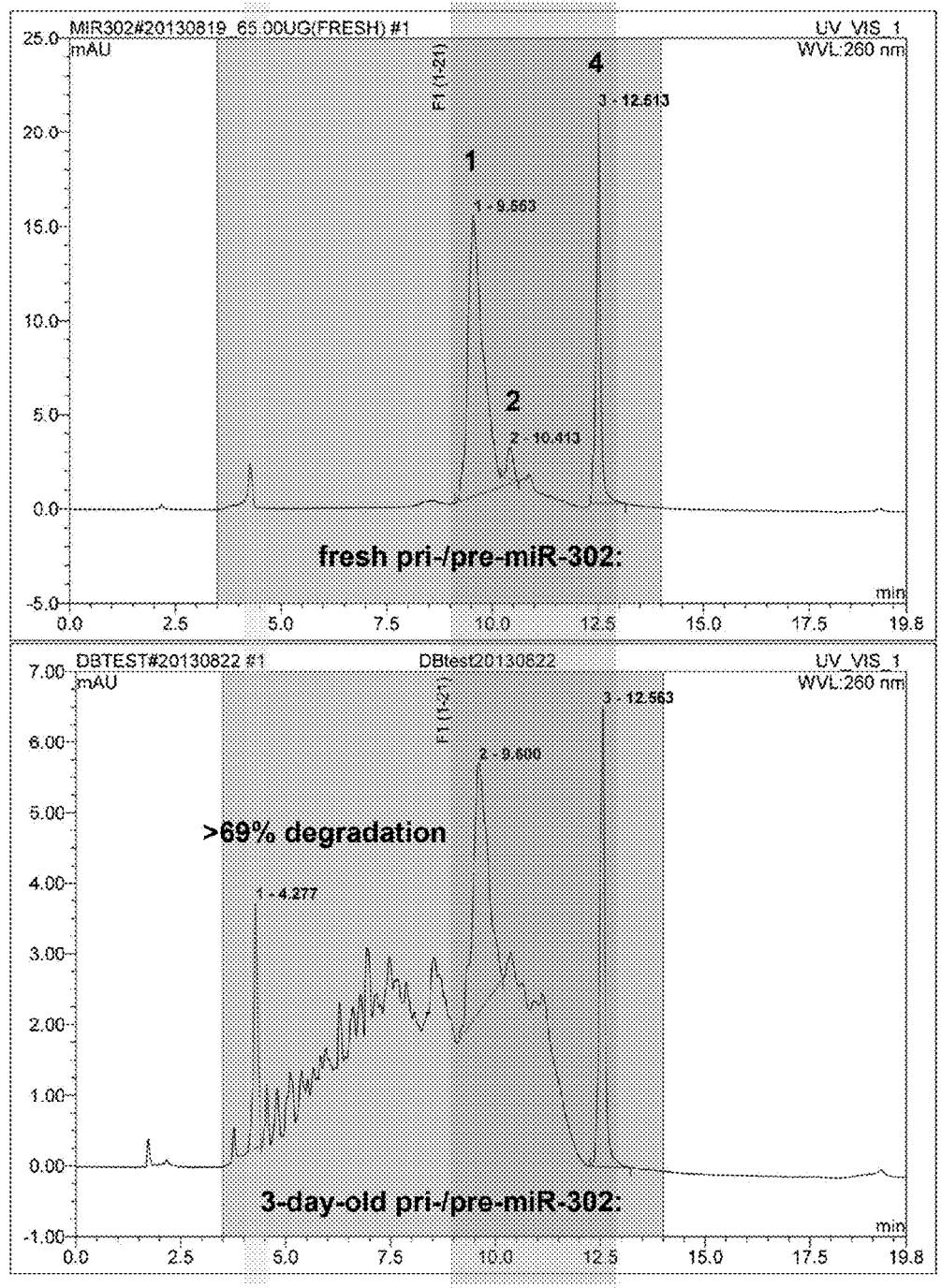
Figure 2C:
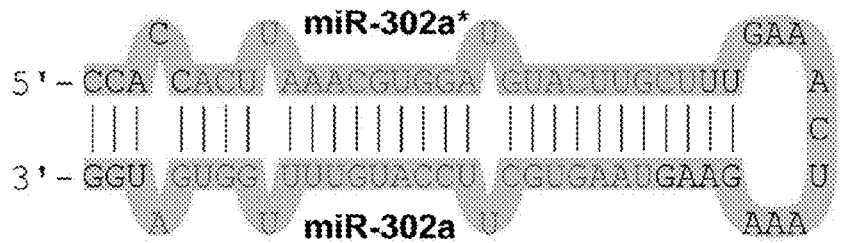
Figure 2C:
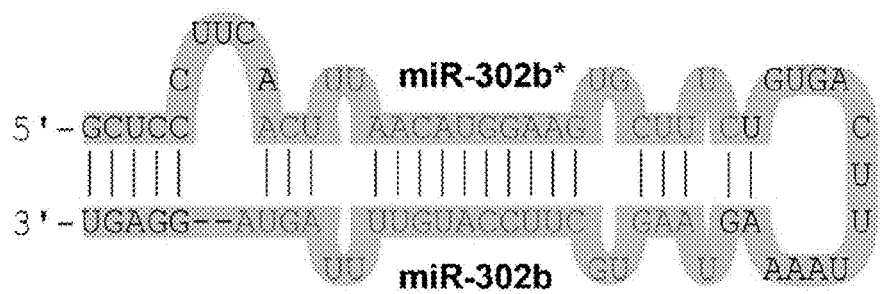
Figure 2C:
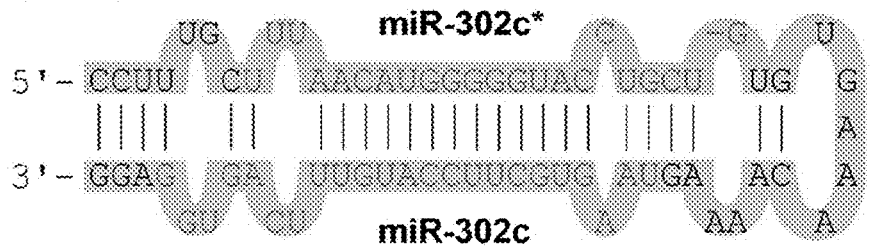
Figure 2C:
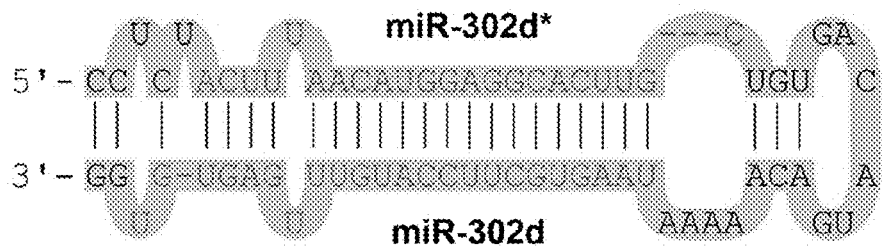
Figure 8:
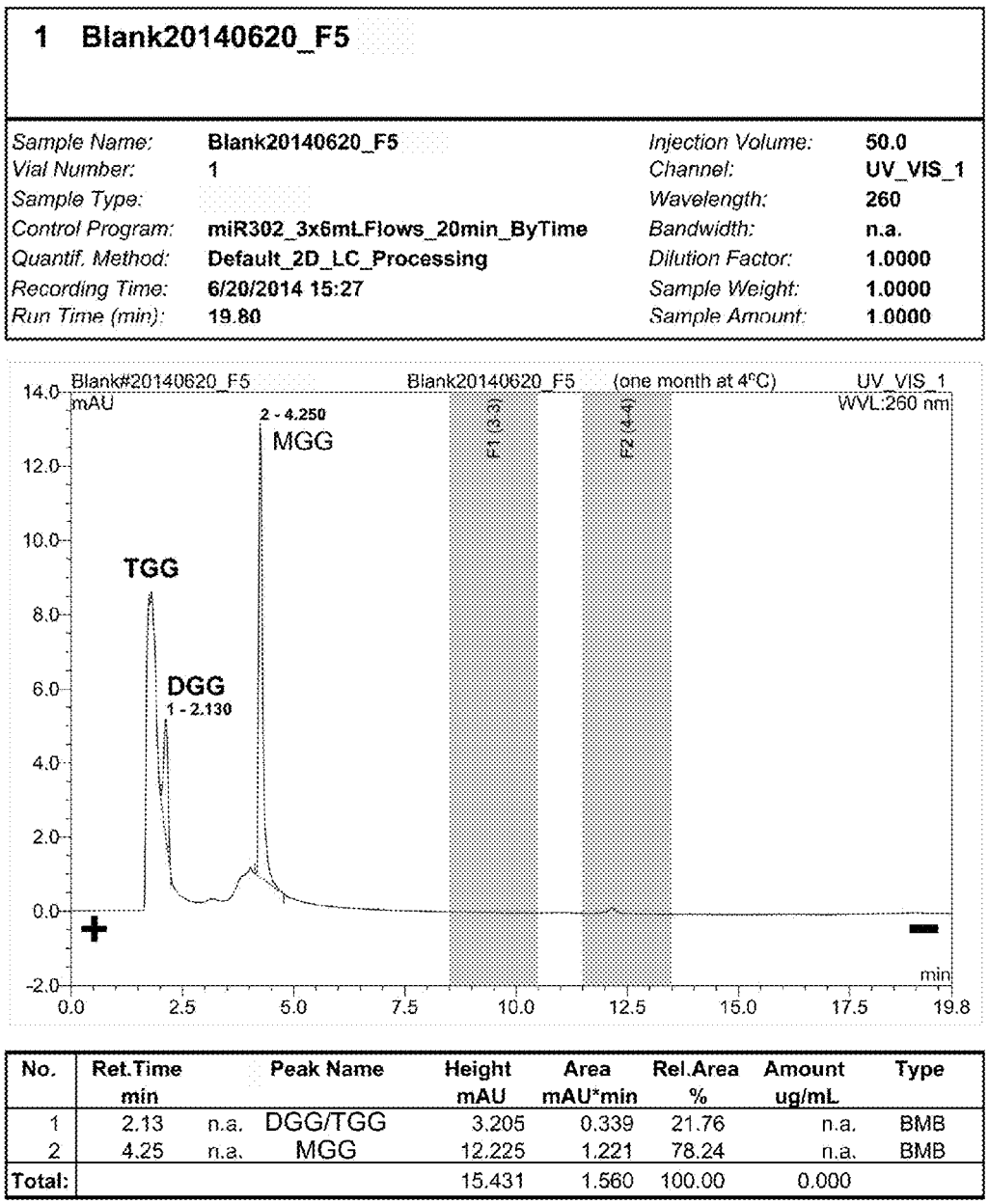
FIG. 8 shows the separation of DGG/TGG from MGG using HPLC purification.

A reverse-phase HPLC method was developed for analyzing the purity and structural integrity of miR-302 and its precursors (i.e. pri-/pre-miR-302s). HPLC programs were run by an Ultimate 3000 HPLC machine (Thermo Scientific) with a DNA Pac PA-100 column (BioLC Semi-Prep 9×250 mm) at a flow rate of 3.6 ml/min. Starting buffer was 50 mM Tris-HCl (pH7.6) and mobile buffer was 50 mM Tris-HCl (pH7.6) with 500 mM sodium perchlorate. Signals of RNAs and DNAs were measured with an UV detector at 260 nm. The results were shown in FIGS. 2A and 2D as well as FIG. 8.

5. MicroRNA (miRNA) Microarray Analysis

Figure 3A:
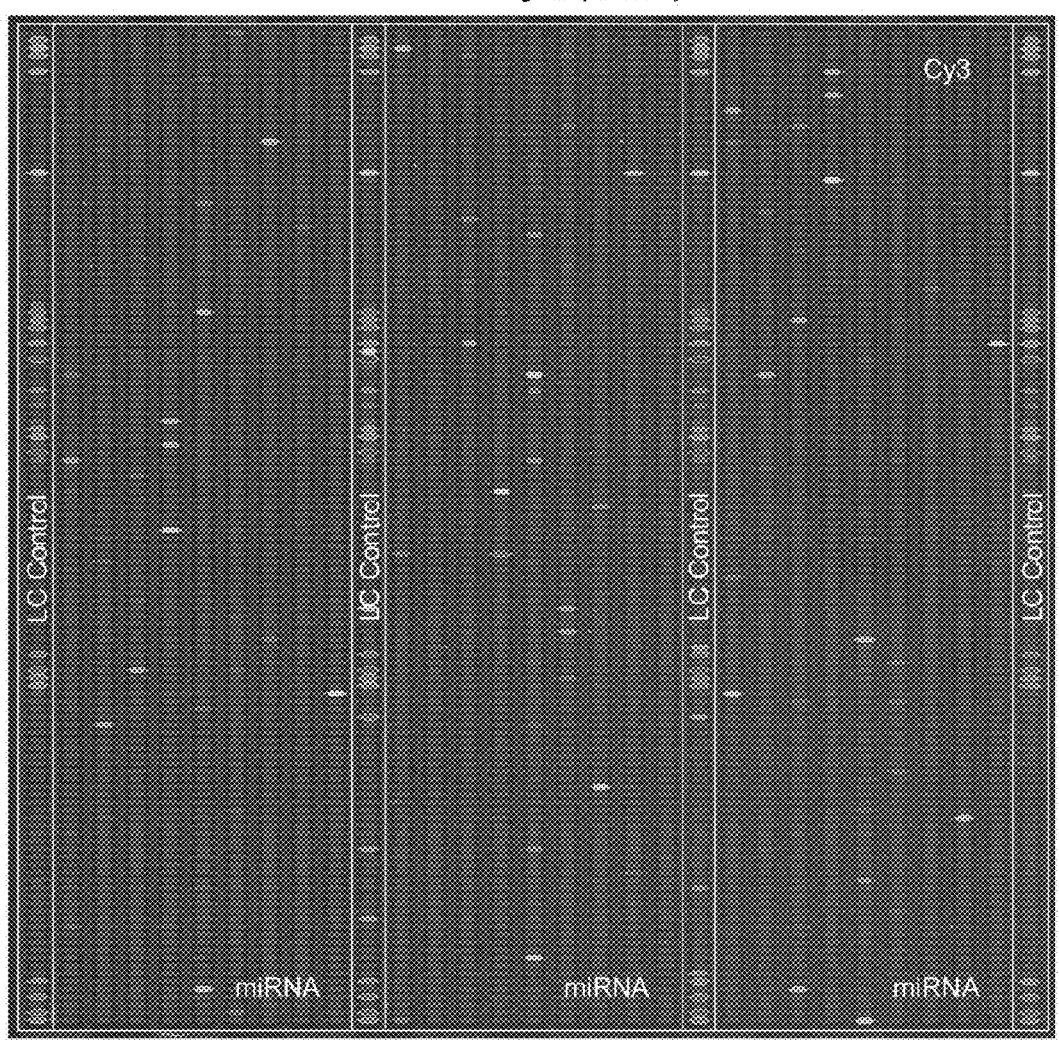
FIGS. 3A and 3B show the results of microRNA (miRNA) microarray analyses using small RNAs extracted from either non-treated blank keratinocytes or sugar alcohol (DGG/TGG)-mediated miR-302-transfected keratinocytes.
Figure 3B:
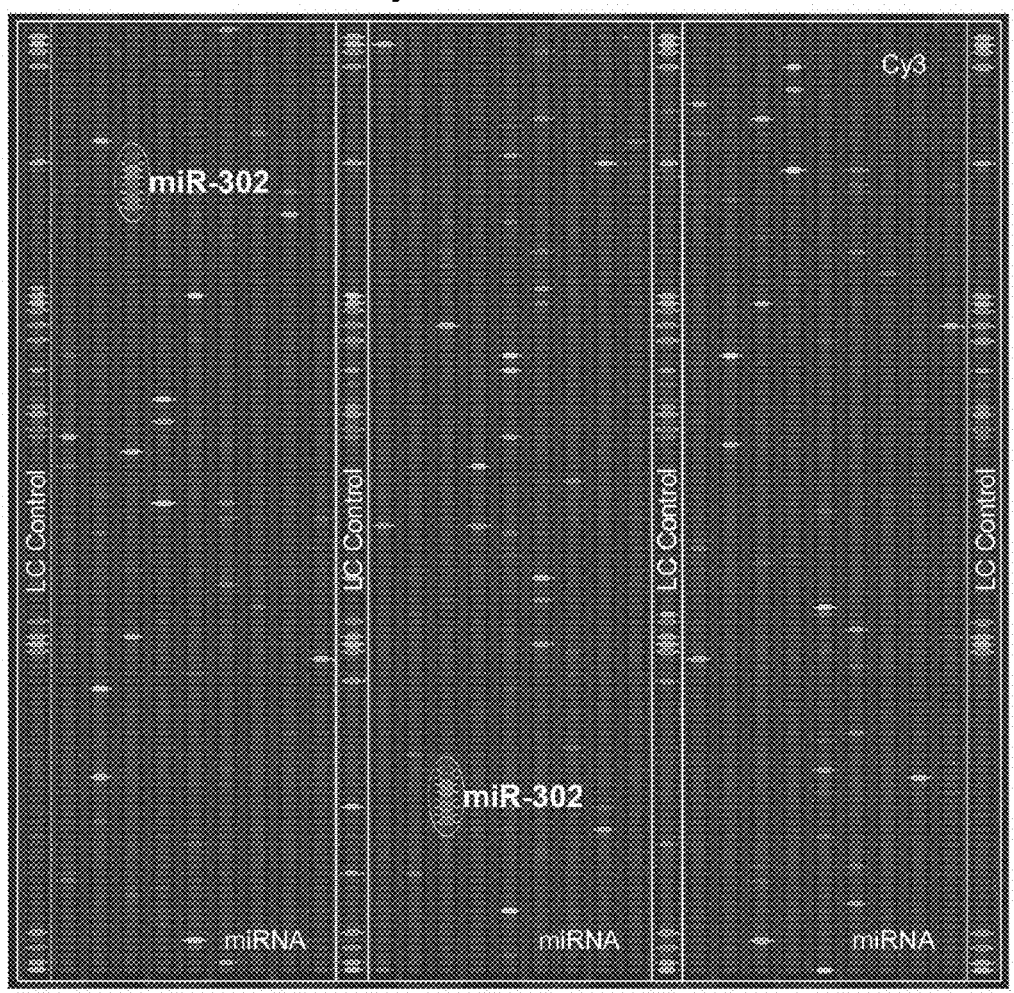
Figure 4A:
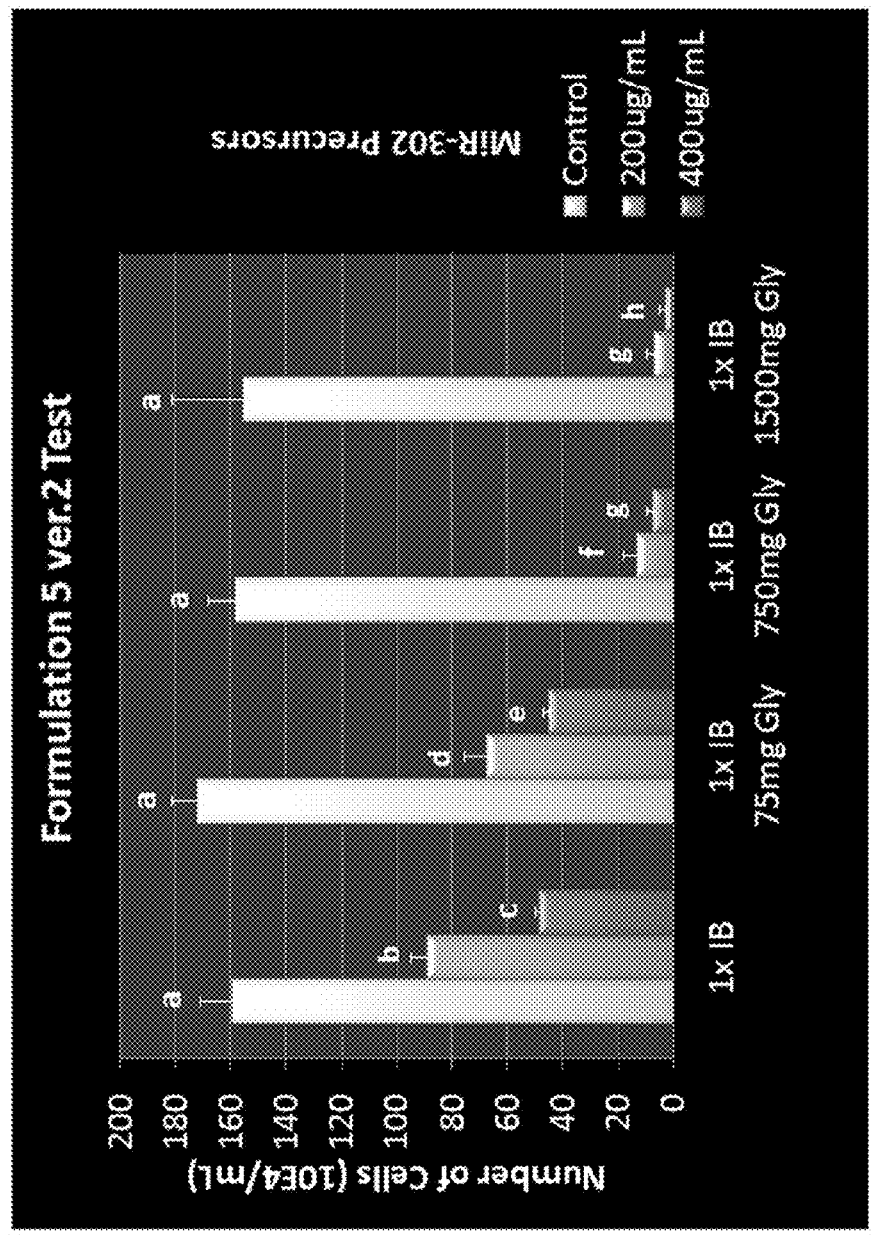
Figure 4B:
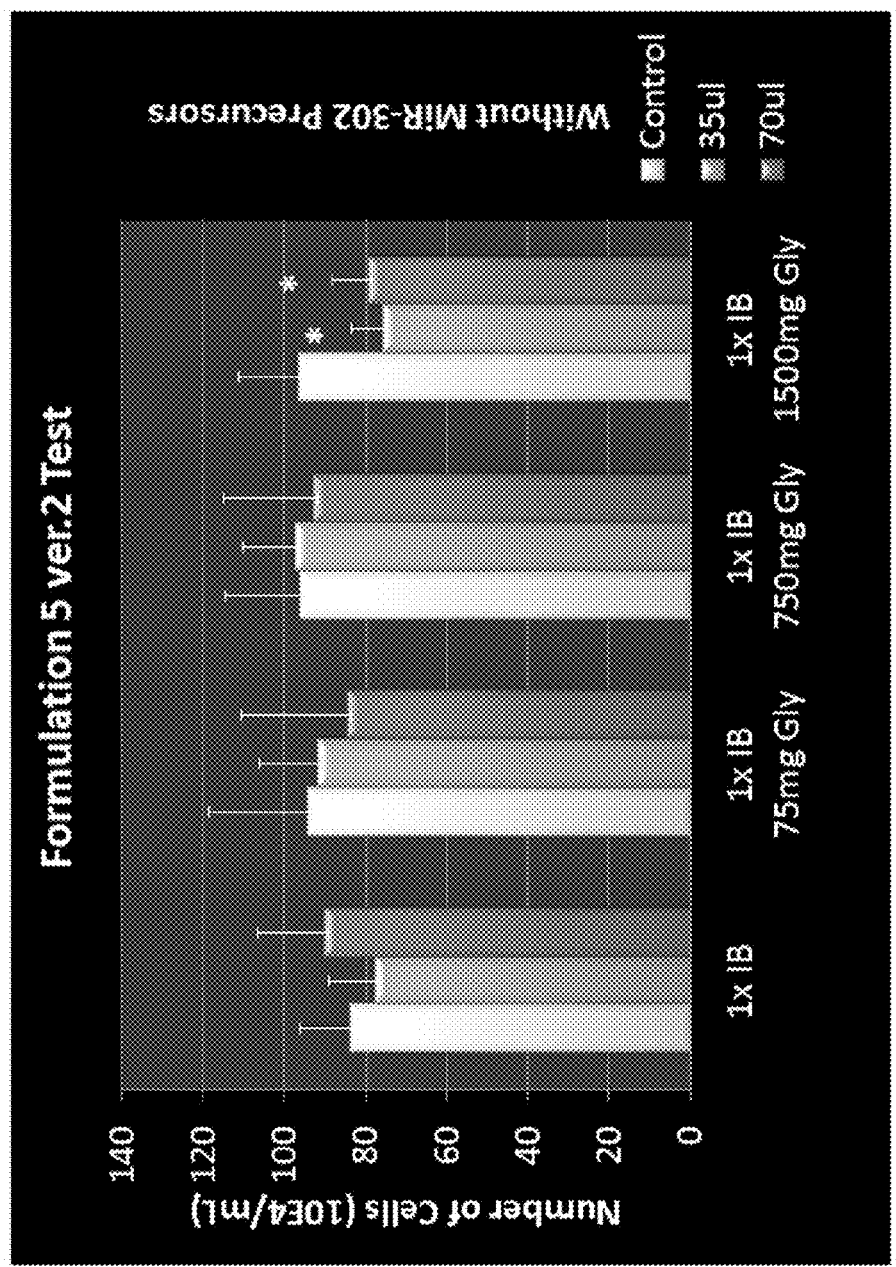

At about 70% confluency, small RNAs from each cell culture were isolated, respectively, using the mirVana™ miRNA isolation kit (Ambion). The purity and quantity of the isolated RNAs were assessed, using 1% formaldehyde-agarose gel electrophoresis and spectrophotometer measurement (Bio-Rad), and then immediately frozen in dry ice and submitted to LC Sciences (San Diego, Calif.) for miRNA microarray analyses. Each microarray chip was hybridized with a single sample labeled with either Cy3 or Cy5 or a pair of samples labeled with Cy3 and Cy5, respectively. Background subtraction and normalization were performed as manufacturer's suggestions. For a dual sample assay, a p-value calculation was performed and a list of differentially expressed transcripts more than 3-fold (yellow-red signals) was produced. The final microarray results were shown in FIGS. 3A and 3B, which compared the RNAs extracted from non-treated blank keratinocytes (3A) to those extracted from DGG/TGG-mediated miR-302-transfected keratinocytes (3B).

6. In Vivo Bio-Imaging of Sugar Alcohol-Delivered siRNA Distribution

Figure 5:
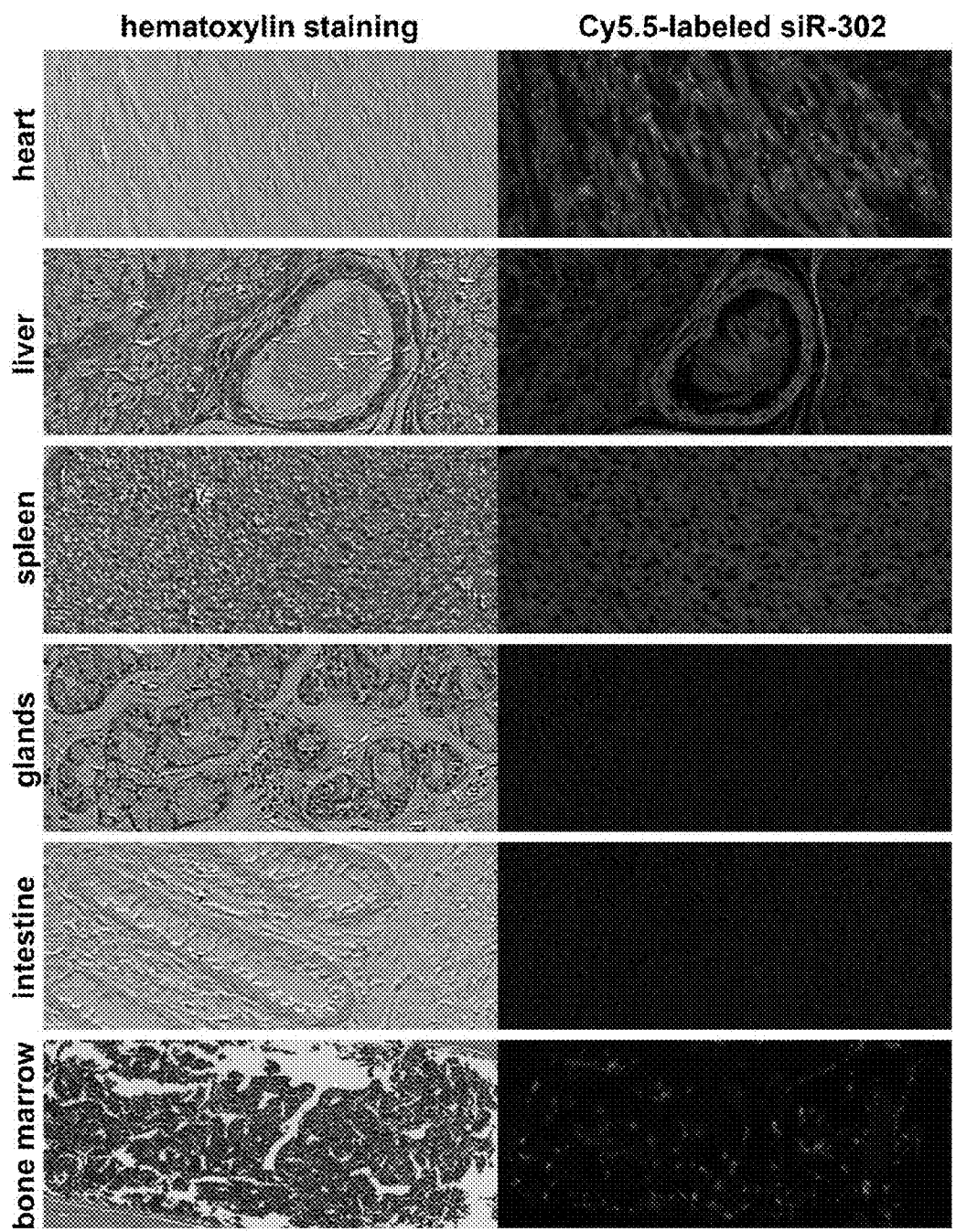
FIG. 5 shows the in-vivo distribution of Cyanine 5.5 (Cy5.5)-labeled miR-302 mimics (siR-302) in mouse, wherein siR-302 consists of synthetic siRNA duplexes formed by the hybrids of 5'-Cy5.5-UAAGUGCUUC CAUGUUUAG UGU-3' (SEQ.ID.NO.6) and 5'-Cy5.5-ACAC-UAAAAC AUGGAAGCAC UUA-3' (SEQ.ID.NO.7) in order to mimic the stem arm portion of pre-miR-302a/c.
Figure 6:
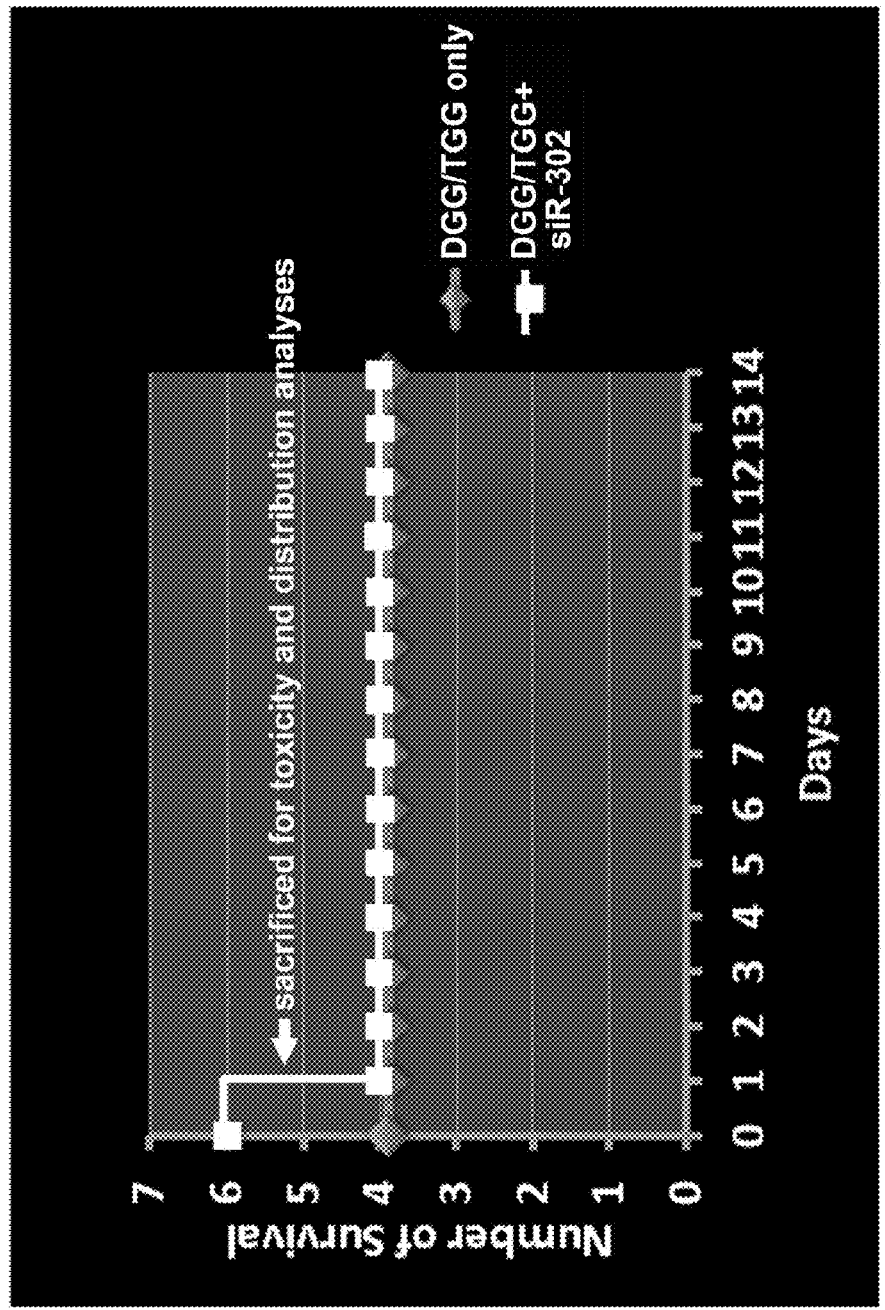
FIG. 6 shows the survival rates of mice subjected to tail vein injection of either glycylated sugar alcohols only (200 μl of 1.0 M DGG/TGG; n=4) or glycylated sugar alcohol-encapsulated siR-302 (200 μg of siR-302 in 200 μl of 1.0 M DGG/TGG; n=4 after two sacrifices for toxicity examination and in-vivo siR-302 distribution analyses (6-2)).

To test the in-vivo deliver efficiency and toxicity of glycylated sugar alcohol-encapsulated nucleic acid compositions, we injected 200 µg of synthetic siR-302 (from Example 1) dissolved in 200 µl of 1.0 M DGG/TGG solution into each of C57BL/6J strain mice via tail vein injection. Approximately 24 hours post-injection, we sacrificed two mice for observing the DGG/TGG-delivered siR-302 distribution in vivo. Since these siR-302 molecules were labeled with infra-red fluorescent dye Cy5.5, we could directly observe their in-vivo distribution using a bio-imaging system and/or their fluorescent signals in mouse tissue sections under a fluorescent microscope. The results were shown in FIG. 5.

7. Statistic Analysis

Any change over 75% of signal intensity was considered as a positive result, which in turn was analyzed and presented as mean±SE. Statistical analysis of data was performed by one-way ANOVA. When main effects were significant, the Dunnett's post-hoc test was used to identify the groups that differed significantly from the controls. For pairwise comparison between two treatment groups, the two-tailed student t test was used. For experiments involving more than two treatment groups, ANOVA was performed followed by a post-hoc multiple range test. Probability values of $p<0.05$ was considered significant. All p values were determined from two-tailed tests.

REFERENCES

1. Immordino M L, Dosio F, Cattel L. (2006) Int J Nanomedicine. Stealth liposomes: review of the basic science, rationale, and clinical applications, existing and potential. *Int J Nanomedicine* 1, 297-315.
2. WIPO Patent No. WO2011143237 to Meyering.
3. Pereira G R, Collett J H, Garcia S B, Thomazini J A, Bentley M V L B. (2002) Glycerol monooleate/solvents systems for progesterone transdermal delivery: in vitro permeation and microscopic studies. *Brazilian Journal of Pharmaceutical Sciences* 38, 55-62.
4. Zhen G, Hinton T M, Muir B W, Shi S, Tizard M, McLean K M, Hartley P G, Gunatillake P. (2012) Glycerol monooleate-based nanocarriers for siRNA delivery in vitro. *Mol Pharm.* 9, 2450-2457.
5. Gao H, Elsabahy M, Giger E V, Li D, Prud'homme R E, Leroux J C. (2010) Aminated linear and star-shape poly (glycerol methacrylate)s: synthesis and self-assembling properties. *Biomacromolecules.* 11, 889-895.
6. Gao H, Lu X, Ma Y, Yang Y, Li J, Wu G, Wang Y, Fan Y, Ma J. (2011) Amino poly(glycerol methacrylate)s for oligonucleic acid delivery with enhanced transfection efficiency and low cytotoxicity. *Soft Matter* 7, 9239-9247.
7. European Patent Application No. EP92116370.5 to Nair.
8. WIPO Patent No. WO2009029046 to Kim.
9. U.S. Pat. No. 5,618,933 to Dordick.
10. Banerjee G, Nandi G, Mahato S B, Pakrashi A, Basu M K. (1996) Drug delivery system: targeting of pentamidines to specific sites using sugar grafted liposomes. *Journal of Antimicrobial Chemotherapy* 38, 145-150.
11. WIPO Patent No. WO 2002032398 to Kohane.
12. Davis B G and Robinson M K. (2002) Drug delivery systems based on sugar-macromolecule conjugates. *Current Opinion in Drug Discovery & Development* 5, 279-288.
13. Blanchfield J and Toth I. (2004) Lipid, sugar and liposaccharide based delivery systems 2. *Current Medicinal Chemistry* 11, 2375-2382.
14. Morris G A, Kok M S, Harding S E, Adams G G. (2010) Polysaccharide drug delivery systems based on pectin and chitosan. *Biotechnology and Genetic Engineering Reviews* 27, 257-284.
15. Cuña M, Alonso-Sandel M, Remuñán-López C, Pivel J P, Alonso-Lebrero J L, Alonso M J. (2006) Development of phosphorylated glucomannan-coated chitosan nanoparticles as nanocarriers for protein delivery. *J Nanosci Nanotechnol.* 6, 2887-2895.
16. Graf A, Ablinger E, Peters S, Zimmer A, Hook S, Rades T. (2008) Microemulsions containing lecithin and sugar-based surfactants: nanoparticle templates for delivery of proteins and peptides. *Int J Pharm.* 350, 351-360.
17. Davis M E, Zuckerman J E, Choi C H, Seligson D, Tolcher A, Alabi C A, Yen Y, Heidel J D, Ribas A. (2010) Evidence of RNAi in humans from systemically administered siRNA via targeted nanoparticles. *Nature* 464, 1067-1070.
18. Bhatia S, Mohr A, Mathur D, Parmar V S, Haag R, Prasad A K. (2011) Biocatalytic route to sugar-PEG-based polymers for drug delivery applications. *Biomacromolecules* 12, 3487-3498.
19. Ellis G A, Palte M J, Taines R T. (2012) Boronate-Mediated Biologic Delivery. *Journal of American Chemical Society* 134, 3631-3634.
20. Lin S L, Jiang A, Chang D, and Ying S Y. (2008) Loss of mir-146a function in hormone-refractory prostate cancer. *RNA* 14, 417-424.
21. Lin S L, Chang D, Chang-Lin S, Lin C H, Wu D T S, Chen D T, and Ying S Y. (2008) Mir-302 reprograms human skin cancer cells into a pluripotent ES-cell-like state. *RNA* 14, 2115-2124.
22. Lin S L, Chang D, Ying S Y, Leu D, and Wu D T S. (2010) MicroRNA miR-302 inhibits the tumorigenecity of human pluripotent stem cells by coordinate suppression of CDK2 and CDK4/6 cell cycle pathways. *Cancer Res.* 70, 9473-9482.

23. Chen S K J and Lin S L. (2013) Recent patents on microRNA-induced pluripotent stem cell generation. *Recent Patents on Regenerative Medicine* 3, 5-16.

The invention claimed is:

1. A method for formulating nucleic acid compositions with sugars and sugar alcohols into stable complexes for both in-vitro and in-vivo delivery into mammalian cells, comprising:
   (a) providing at least a nucleic acid composition with at least a negative charge;
   (b) preparing at least one sugar or sugar alcohol composition modified by glycylation to form a glycylated sugar or sugar alcohol composition; wherein said glycylation is a chemical reaction that replaces the hydroxyl (HO—) groups of a sugar alcohol or sugar with glycyl ($NH_2CH_2COO$—) groups and thus results in the formation of an ether (R—O—R) linkage between each OH-removed carbon of the sugar alcohol or sugar and the glycyl group and wherein said glycylation reaction occurs under a pH value ranged from 2.5 to 8.0 at a temperature over 45° C. for at least 30 minutes; wherein the sugar alcohol has a formula of $H(HCHO)_{n+1}H$, and the sugar has a formula of $H(HCHO)_nHCO$, and wherein the optimal concentration of said glycyl group is ranged from 0.05 to 3.0 M for mixing with per 1.0 M of sugar alcohol in the glycylation reaction; and
   (c) mixing the nucleic acid composition from (a) and the glycylated sugar or sugar alcohol composition from (b) together under a condition below pH 8.0 to form at least a delivery complex.

2. The method as defined in claim 1, wherein said nucleic acid composition is RNA.

3. The method as defined in claim 2, wherein said nucleic acid composition is small hairpin RNAs (shRNA).

4. The method as defined in claim 1, wherein said sugar or sugar alcohol composition is glycerol (glycerin).

5. The method as defined in claim 1, wherein said at least one modified sugar or sugar alcohol composition by glycylation contains a mixture of diglycylglycerol and triglycylglyceride.

6. The method as defined in claim 1, wherein said modified sugar or sugar alcohol composition by glycylation is positively charged.

7. The method as defined in claim 1, wherein said modified sugar or sugar alcohol composition is in solution and has a concentration ranged from about 0.1 μM to about 10 M.

8. The method as defined in claim 1, wherein a maximal solubility of said nucleic acid composition in the modified sugar or sugar alcohol composition in a solution is up to 15 mg/mL.

9. The method as defined in claim 1, wherein said modified sugar or sugar alcohol composition protects said nucleic acid compositions from degradation.

10. The method as defined in claim 1, wherein said modified sugar or sugar alcohol composition enhances the delivery efficiency of said nucleic acid compositions into mammalian cells in vitro as well as in vivo.

11. The method as defined in claim 1, wherein said condition is a pH value below 8.0.

12. The method as defined in claim 11, wherein said condition is a pH value between about pH 2.5 and about pH 7.0.

13. The method as defined in claim 1, wherein said deliver complex is formed by the ionic or electrostatic affinity occurring between the modified sugar or sugar alcohol and the nucleic acid composition.

14. The method as defined in claim 1, wherein said nucleic acid composition is cosmetic, pharmaceutical or therapeutic DNA or RNA.

15. The method as defined in claim 1, wherein said glycylation is a chemical reaction in that at least one hydroxyl group of the sugar or the sugar alcohol is replaced by at least one glycyl group from a glycine or a glycylated amino acid.

16. A method for delivering nucleic acids into cells in vitro as well as in vivo, comprising:
mixing at least a glycerol (glycerin) composition with hydroxyl group, at least one amino acid with a structure of glycyl group, and at least a nucleic acid composition, wherein said mixing forms at least one glycylated glycerol (glycerin) composition which interacts with said nucleic acid composition via ionic or electrostatic affinity and forms a delivery complex at a pH value below 8.0,
wherein said glycylated glycerol (glycerin) composition is formed by a glycylation reaction that replaces the hydroxyl (HO—) groups of said glycerol (glycerin) composition with glycyl ($NH_2CH_2COO$—) groups and thus results in the formation of an ether (R—O—R) linkage between each OH-removed carbon of the glycerol (glycerin) composition and the glycyl group and wherein said glycylation reaction occurs under a pH value ranged from 2.5 to 8.0 at a temperature over 45° C. for at least 30 minutes; and wherein the optimal concentration of said glycyl group in the glycylation reaction is ranged from 0.05 to 3.0 M for mixing with per 1.0 M of sugar alcohol in the glycylation reaction.

17. The method of claim 16, wherein said amino acid with said structure of glycyl group is glycine or a glycylated amino acid.

18. The method of claim 16, wherein said nucleic acid composition is RNA.

19. The method of claim 18, wherein said nucleic acid composition is small hairpin RNAs (shRNA).

20. The method of claim 16, further comprising mixing 0.3 M fructose and 0.9% (w/v) sodium chloride (NaCl) in a solution form with said glycylated glycerol (glycerin) composition.

21. The method of claim 16, wherein said mixture is further in a solution having a pH value below pH 8.0.

22. The method of claim 21, wherein said pH value is pH 2.5 to pH 7.0.

23. The method of claim 16, wherein said at least one glycylated glycerol (glycerin) composition is selected from the group consisting of monoglycylglycerol, diglycylglycerol and triglycylglyceride.

24. The method of claim 16, wherein a concentration of said glycylated glycerol (glycerin) composition is ranged from about 0.1 μM to about 10 M.

25. The method of claim 16, wherein said glycylated glycerol (glycerin) composition is positively charged.

26. The method of claim 16, wherein said nucleic acid composition is negatively charged.

27. The method of claim 16, wherein a maximal solubility of said nucleic acid composition in a solution containing the mixture is up to 15 mg/mL.

28. The method of claim 16, wherein said glycylated glycerol (glycerin) composition protects said nucleic acid compositions from degradation.

29. The method of claim 16, wherein said glycylated glycerol (glycerin) composition enhances the delivery efficiency of said nucleic acid compositions into cells in vitro as well as in vivo.

30. The method of claim 16, wherein said nucleic acid composition in said delivery complex is cosmetic, pharmaceutical and therapeutic DNA or RNA.

* * * * *

SEQUENCE LISTING

<160> NUMBER OF SEQ ID NOS: 7

<210> SEQ ID NO 1
<211> LENGTH: 720
<212> TYPE: DNA
<213> ORGANISM: Artificial Sequence
<220> FEATURE:
<223> OTHER INFORMATION: chemical synthesis

<400> SEQUENCE: 1

```
aattttttc ttctaaagtt atgccatttt gttttctttc tcctcagctc taaatactct      60
gaagtccaaa gaagttgtat gttgggtggg ctcccttcaa ctttaacatg gaagtgcttt     120
ctgtgacttt aaaagtaagt gcttccatgt tttagtagga gtgaatccaa tttacttctc     180
caaaatagaa cacgctaacc tcatttgaag ggatcccctt tgctttaaca tggggtacc      240
tgctgtgtga aacaaaagta agtgcttcca tgtttcagtg gaggtgtctc caagccagca     300
cacctttgt tacaaaattt ttttgttatt gtgttttaag gttactaagc ttgttacagg      360
ttaaaggatt ctaactttt ccaagactgg gctcccacc acttaaacgt ggatgtactt       420
gctttgaaac taagaagta agtgcttcca tgttttggtg atggtaagtc ttcttttac       480
attttatta ttttttaga aaataacttt attgtattga ccgcagctca tatatttaag       540
ctttattttg tattttaca tctgttaagg ggcccctct actttaacat ggaggcactt      600
gctgtgacat gacaaaaata agtgcttcca tgtttgagtg tggtggttcc tacctaatca    660
gcaattgagt taacgcccac actgtgtgca gttcttggct acaggccatt actgttgcta    720
```

<210> SEQ ID NO 2
<211> LENGTH: 69
<212> TYPE: RNA
<213> ORGANISM: Artificial Sequence
<220> FEATURE:
<223> OTHER INFORMATION: chemical synthesis

<400> SEQUENCE: 2

```
ccaccacuua aacguggaug uacuugcuuu gaaacuaaag aaguaagugc uuccauguuu     60
uggugaugg                                                            69
```

<210> SEQ ID NO 3
<211> LENGTH: 73
<212> TYPE: RNA
<213> ORGANISM: Artificial Sequence
<220> FEATURE:
<223> OTHER INFORMATION: chemical synthesis

<400> SEQUENCE: 3

```
gcucccuuca acuuuaacau ggaagugcuu ucgugacuu uaaaaguaag ugcuuccaug      60
uuuuaguagg agu                                                       73
```

<210> SEQ ID NO 4
<211> LENGTH: 68
<212> TYPE: RNA
<213> ORGANISM: Artificial Sequence
<220> FEATURE:
<223> OTHER INFORMATION: chemical synthesis

<400> SEQUENCE: 4

-continued

```
ccuuugcuuu aacauggggg uaccugcugu gugaaacaaa aguaagugcu uccauguuuc      60
aguggagg                                                              68

<210> SEQ ID NO 5
<211> LENGTH: 68
<212> TYPE: RNA
<213> ORGANISM: Artificial Sequence
<220> FEATURE:
<223> OTHER INFORMATION: chemical synthesis

<400> SEQUENCE: 5
ccucuacuuu aacauggagg cacuugcugu gacaugacaa aaauaagugc uuccauguuu      60
gagugugg                                                              68

<210> SEQ ID NO 6
<211> LENGTH: 23
<212> TYPE: RNA
<213> ORGANISM: Artificial Sequence
<220> FEATURE:
<223> OTHER INFORMATION: chemical synthesis

<400> SEQUENCE: 6
uaagugcuuc cauguuuag ugu                                              23

<210> SEQ ID NO 7
<211> LENGTH: 23
<212> TYPE: RNA
<213> ORGANISM: Artificial Sequence
<220> FEATURE:
<223> OTHER INFORMATION: chemical synthesis

<400> SEQUENCE: 7
acacuaaaac auggaagcac uua                                             23
```